United States Patent
Nishino et al.

(10) Patent No.: US 9,012,166 B2
(45) Date of Patent: Apr. 21, 2015

(54) METHOD FOR ASSAYING HISTONE METHYLATION ENZYME ACTIVITY

(75) Inventors: Norikazu Nishino, Fukuoka (JP);
Yasushi Takemoto, Saitama (JP);
Akihiro Ito, Saitama (JP); Minoru Yoshida, Tokyo (JP)

(73) Assignee: Kyushu Institute of Technology, Fukuoka (JP)

(*) Notice: Subject to any disclaimer, the term of this patent is extended or adjusted under 35 U.S.C. 154(b) by 93 days.

(21) Appl. No.: 13/639,334

(22) PCT Filed: Apr. 15, 2011

(86) PCT No.: PCT/JP2011/002231
§ 371 (c)(1),
(2), (4) Date: Oct. 4, 2012

(87) PCT Pub. No.: WO2011/132392
PCT Pub. Date: Oct. 27, 2011

(65) Prior Publication Data
US 2013/0029878 A1    Jan. 31, 2013

(30) Foreign Application Priority Data

Apr. 19, 2010 (JP) .................................. 2010-096496
Sep. 9, 2010 (JP) .................................. 2010-202484

(51) Int. Cl.
| | | |
|---|---|---|
| G01N 21/78 | (2006.01) | |
| C12Q 1/37 | (2006.01) | |
| C12Q 1/48 | (2006.01) | |
| G01N 33/68 | (2006.01) | |
| C07D 311/18 | (2006.01) | |
| C07D 311/82 | (2006.01) | |
| C07D 473/32 | (2006.01) | |

(52) U.S. Cl.
CPC .. C12Q 1/37 (2013.01); C12Q 1/48 (2013.01); G01N 2500/00 (2013.01); G01N 33/6875 (2013.01); C07D 311/18 (2013.01); C07D 311/82 (2013.01); C07D 473/32 (2013.01)

(58) Field of Classification Search
CPC ......... G01N 33/6875; C12Q 1/48; C12Q 1/37
See application file for complete search history.

(56) References Cited

U.S. PATENT DOCUMENTS 7,256,013 B2 * 8/2007 Tamai et al. ............... 435/24

FOREIGN PATENT DOCUMENTS

| JP | 2001149081 | 6/2001 |
| JP | 2003221398 | 8/2003 |
| JP | 2003221399 | 8/2003 |
| JP | 20094267043 | 2/2009 |

OTHER PUBLICATIONS

Wegener et al., A fluorogenic histone deacetylase assay well suited for high-throughput activity screening, 2003, Chemistry & Biology 10(1): 61-68.*
European Search Report, EP 11771735.5, dated Jan. 8, 2014.
Collazo, Evys, et al., "A coupled fluorescent assay for histone methyltransferases," Analytical Biochemistry (Jul. 1, 2005 vol. 342, No. 1, pp. 86-92.
Wilson, Jonathan R., et al., "Crystal Structure and Functional Analysis of the Histone Methyltransferase SET7/9," Cell (Oct. 4, 2002) vol. 111, No. 1, pp. 105-115.
Schneider, Robert, et al. "Unsafe SETs: histone lysine methyltransferases and cancer," Trends in Biochemical Sciences, (2002) 27:8, 396-402.
Baylin, Stephen B., et al. "Epigenetic gene silencing in cancer—a mechanism for early oncogenic pathway addiction?" Nature Reviews:Cancer (2006) 6:107-.
Yoo, Christine B., et al., "Epigenetic therapy of cancer: past, present and future," Nature Review:Drug Discovery (2006) 5:37-50.
Fraga, Mario F, et al., "Loss of acetylation at Lys16 and trimethylation at Lys20 of histone H4 is a common hallmark of human cancer," Nature Genetics (2005) 37:4 391-400.
Saveliev, Alexander, et al., "DNA triplet repeats mediate heterochromatin-protein-1-sensitive variegated gene silencing," Nature (2003) 422:909-.
Shi, Yan, et al., "Induction of Pluripotent Stem Cells from Mouse Embryonic Fibroblasts by Oct4 and Klf4 with Small Molecule Compounds," Cell Stem Cell (2006) 3:568-574.
Greiner, Dorothea, et al., "Identification of a specific inhibitor of the histone methyltransferase SU(VAR)3-9," Nature Chemical Biology (2005) 1:3 143-145.
Kubicek, Stefan, et al., "Reversal of H3K9me2 by a Small-Molecule Inhibitor for the G9a Histone Methyltransferase," Molecular Cell (2007) 25:473-481.
Joys, Terence M., et al., "The Susceptability to Tryptic Hyrolysis of Peptide Bonds involving e-N-Methyllysine," Biochimica et Biophysica Acta (1979) 581:360-362.
Poncz, Louis, et al., "The Resistance to Trypic Hydrolysis of Peptide Bonds Adjacent to Ne,N-Dimethyllysyl Residues," The Journal of Biological Chemistry (1983) 258:3 1844-1850.

* cited by examiner

*Primary Examiner* — Robert Yamasaki
(74) *Attorney, Agent, or Firm* — Chainey P. Singleton; Edwin S. Flores; Chalker Flores, LLP

(57) ABSTRACT

Provided are a method for measuring histone methyltransferase activity, a method for screening for compounds that inhibit histone methyltransferase activity, a reagent kit for measuring histone methyltransferase activity, and a kit for screening for compounds that inhibit histone methyltransferase activity. A substrate compound represented by general formula (I): $R_1$-X-K-$R_2$ (I), or a salt thereof, wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue, wherein the cleavage of the amide bond by peptidase changes the fluorescence property or chromogenic property of the dye label, and the methylation of the ε amino group of the lysine residue by the histone methyltransferase decreases susceptibility to peptidase, is used.

6 Claims, 21 Drawing Sheets

Figure 1

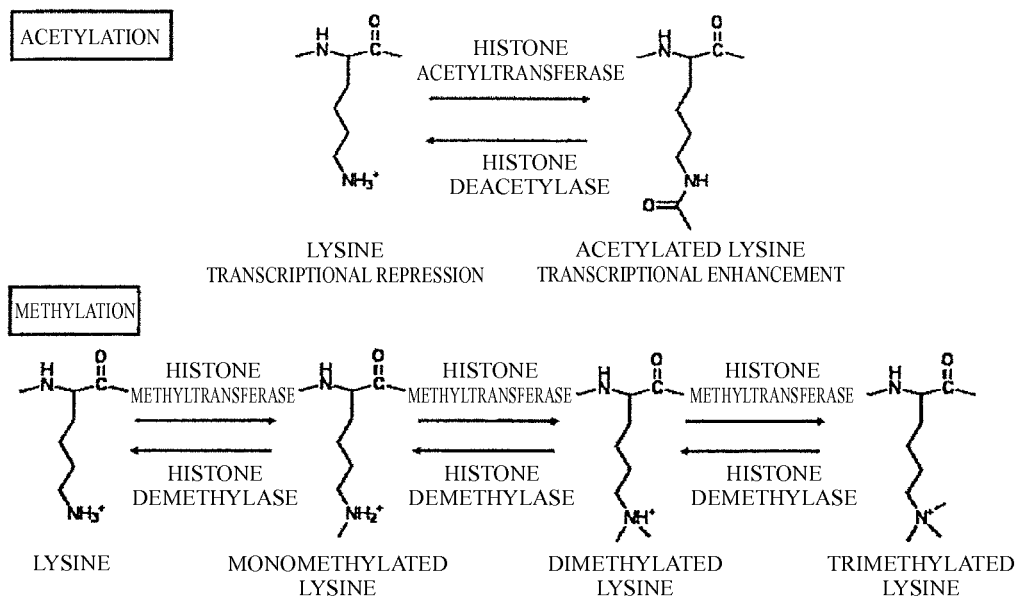

Figure 2

HISTONE (LYSINE) METHYLTRANSFERASE

| LYSINE SITE | INFLUENCE ON TRANSCRIPTION | HISTONE METHYLTRANSFERASE |
|---|---|---|
| HISTONE H3K4 | TRANSCRIPTIONAL ENHANCEMENT | SET1, MLL, SET9 SMYD3, Meisetz |
| HISTONE H3K9 | TRANSCRIPTIONAL REPRESSION | SUV39H1, G9a, GLP, ESET/SETDB1, RIZ |
| HISTONE H3K27 | TRANSCRIPTIONAL REPRESSION | MES-2, EZH2, G9a |
| HISTONE H3K36 | TRANSCRIPTIONAL ENHANCEMENT | NSD1, SMYD2 |
| HISTONE H3K79 | TRANSCRIPTIONAL ENHANCEMENT | DOT1L |
| HISTONE H4K20 | TRANSCRIPTIONAL REPRESSION | SUV4-20H, NSD1 SET8/PR-SET7 |

Figure 5

PROBLEM WITH CONVENTIONAL METHOD

RI METHOD
- A problem with safety due to the use of a radioisotope.
- Relatively many experimental procedures including the adsorption of a reaction product to filter paper and the washing of the filter paper.

ELISA METHOD
- Relatively many experimental procedures including the adsorption of a reaction product to filter paper and the washing of the filter paper.

A new evaluation system having no problem with safety, simple in the experimental procedures and short in time required is useful for screening for compounds.

EXPERIMENTAL METHOD (ELISA METHOD)

| | |
|---|---|
| 2× HMT buffer | 25 µl |
| BSA (150 µg/ml) | 1 µl |
| GST-G9a (0.05 µg/µl) | 1 µl |
| chemical | 1 µl |
| $H_2O$ | 20 µl |

↓ ROOM TEMPERATURE, 1h

| | |
|---|---|
| SAM (0.115 mM) | 1 µl |
| BIOTINYLATED HISTONE H3 PEPTIDE (50µg/ml) | 1 µl |

↓ 37°C, 1 h       Total 50 µl

BOIL AT 95°C FOR 30 MIN AND STOP REACTION
↓
TRANSFER REACTION SOLUTION TO PLATE COATED WITH STREPTAVIDIN.
↓ ROOM TEMPERATURE, 1h
DISCARD REACTION SOLUTION, WASH 3 TIMES FOR 5 MIN WITH 300 µl 1 × PBST, AND THEN ADD ANTI-METHYLATED LYSINE ANTIBODY.
↓ ROOM TEMPERATURE, 1h
DISCARD REACTION SOLUTION, WASH 3 TIMES FOR 5 MIN WITH 300 µl 1 × PBST, AND THEN ADD SECONDARY ANTIBODY.
↓ ROOM TEMPERATURE, 1h
DISCARD REACTION SOLUTION, WASH 5 TIMES FOR 5 MIN WITH 300 µl 1 × PBST, AND THEN ADD CHROMOGENIC SUBSTRATE (TMB PEROXIDASE SUBSTRATE).
↓ ROOM TEMPERATURE, 40min
MEASURE ABSORBANCE (650 nm).

trypsin inhibitor : DERIVED FROM HEN'S EGG (Roche)

Figure 13

EXAMINATION OF SUBSTRATE SPECIFICITY OF HISTONE
METHYLTRANSFERASE USING PEPTIDYL MCA (1)
(SEQUENCE OF PEPTIDYL MCA)

METHYLATED ENZYME     METHYLATION SITE
        G9a       HISTONE H3K9, HISTONE H3K27
        Set9       HISTONE H3K4, p53K372

```
                1    4       9                              27
histone H3    ARTKQTARKSTGGKAPRKQLATKAARK • • •
              ‾‾‾  ‾‾‾‾‾‾‾                    ‾‾‾‾‾‾‾
              1-4   7-9/25-27                  7-9/25-27
                  ‾‾‾‾‾                           ‾‾‾‾‾
                   5-9                            23-27
              ‾‾‾‾‾‾‾‾‾‾                    ‾‾‾‾‾‾‾‾‾‾‾‾
                  1-9                            19-27
```

| PEPTIDYL MCA | AMINO ACID SEQUENCE |
|---|---|
| BocLysMCA | Boc-K-MCA |
| Ac-histone H3 (1-4)-MCA | Ac-ARTK-MCA |
| Ac-histone H3 (5-9)-MCA | Ac-QTARK-MCA |
| Ac-histone H3 (1-9)-MCA | Ac-ARTKQTARK-MCA |
| Ac-hisotne H3 (7-9 / 25-27)-MCA | Ac-ARK-MCA |
| Ac-histone H3 (23-27)-MCA | Ac-KAARK-MCA |
| Ac-histone H3 (19-27)-MCA | Ac-QLATKAARK-MCA |
| Ac-p53 (369-372)-MCA | Ac-LKSK-MCA |

Figure 14

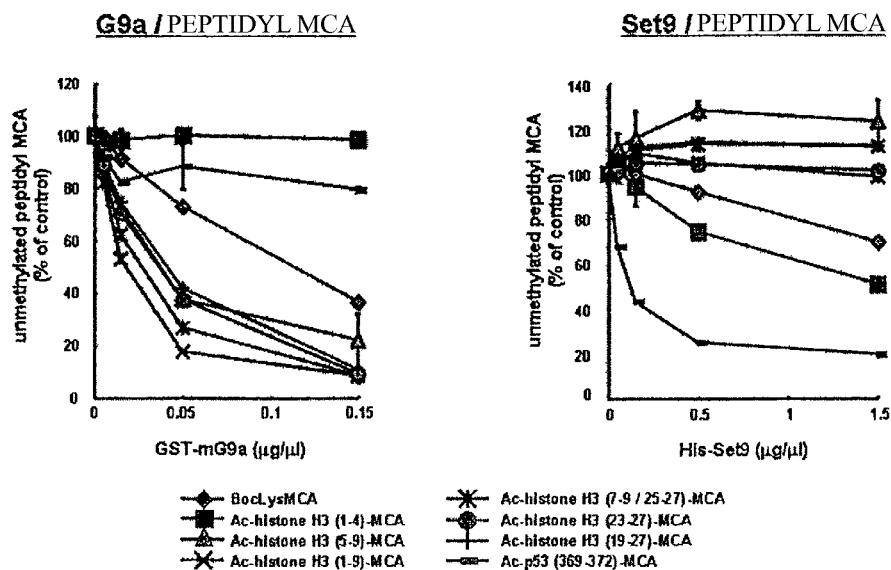

EXAMINATION OF MATRIX SPECIFICITY OF HISTONE
METHYLTRANSFERASE USING PEPTIDYL MCA (1)

Figure 15

EXAMINATION OF MATRIX SPECIFICITY OF HISTONE
METHYLTRANSFERASE USING PEPTIDYL MCA (2)
(SEQUENCE OF PEPTIDYL MCA)

| PEPTIDYL MCA | AMINO ACID SEQUENCE |
|---|---|
| Ac-ERα (299-302)-MCA | Ac-KRSK-MCA |
| Ac-ERα (297-302)-MCA | Ac-MIKRSK-MCA |
| Ac-AR (630-633)-MCA | Ac-RKLK-MCA |
| Ac-AR (628-633)-MCA | Ac-GARKLK-MCA |
| Ac-GR (491-494)-MCA | Ac-RKTK-MCA |
| Ac-GR (489-494)-MCA | Ac-EARKTK-MCA |
| Ac-p53 (369-372)-MCA | Ac-LKSK-MCA |
| Ac-p53 (367-372)-MCA | Ac-SHLKSK-MCA |
| Ac-histone H3 (1-9)-MCA | Ac-ARTKQTARK-MCA |

ERα : estrogen receptor α
AR : androgen receptor
GR : glucocorticoid receptor

Figure 16
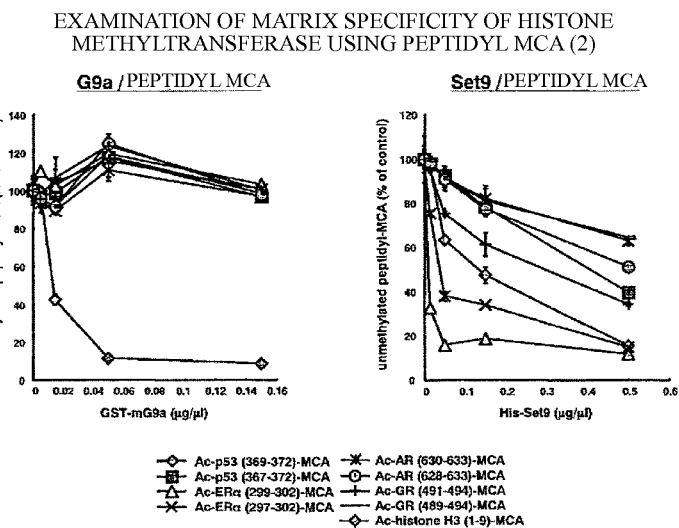
Figure 17
ACTIVITY EVALUATION OF HISTONE METHYLTRANSFERASE
INHIBITOR USING PEPTIDYL MCA
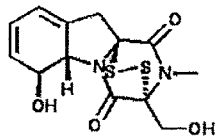
GLIOTOXIN;
INHIBITS THE METHYLATION
ACTIVITY OF G9a BUT DOES NOT
INHIBIT THE METHYLATION
ACTIVITY OF Set 9.
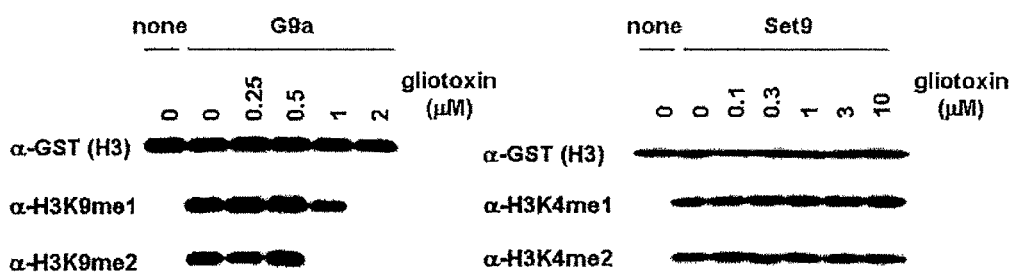

ACTIVITY EVALUATION OF HISTONE METHYLTRANSFERASE
INHIBITOR USING PEPTIDYL MCA
(gliotoxin)

ACTIVITY EVALUATION OF HISTONE METHYLTRANSFERASE
INHIBITOR USING PEPTIDYL MCA
(SAH)

REACTIVITY BETWEEN BocLys(Me)$_n$MCA (n = 0, 1, 2, 3) AND TRYPSIN

REACTIVITY BETWEEN BocLys(Me)$_n$MCA (n = 0, 1, 2, 3) AND LYSYL ENDOPEPTIDASE

```
                           SEQUENCE LISTING

<160> NUMBER OF SEQ ID NOS: 21

<210> SEQ ID NO 1
<211> LENGTH: 4
<212> TYPE: PRT
<213> ORGANISM: Homo sapiens
<220> FEATURE:
<223> OTHER INFORMATION: Inventor: Nishino, Norikazu; Takemoto, Yasushi;
      Ito, Akihiro; Yoshida, Minoru
<220> FEATURE:
<223> OTHER INFORMATION: Human histone H3 (1-4)

<400> SEQUENCE: 1

Ala Arg Thr Lys
1

<210> SEQ ID NO 2
<211> LENGTH: 5
<212> TYPE: PRT
<213> ORGANISM: Homo sapiens
<220> FEATURE:
<223> OTHER INFORMATION: Human histone H3 (5-9)

<400> SEQUENCE: 2

Gln Thr Ala Arg Lys
1               5

<210> SEQ ID NO 3
<211> LENGTH: 9
<212> TYPE: PRT
<213> ORGANISM: Homo sapiens
<220> FEATURE:
<223> OTHER INFORMATION: Human histone H3 (1-9)

<400> SEQUENCE: 3

Ala Arg Thr Lys Gln Thr Ala Arg Lys
1               5

<210> SEQ ID NO 4
<211> LENGTH: 5
<212> TYPE: PRT
<213> ORGANISM: Homo sapiens
<220> FEATURE:
<223> OTHER INFORMATION: Human histone H3 (23-27)

<400> SEQUENCE: 4

Lys Ala Ala Arg Lys
1               5

<210> SEQ ID NO 5
<211> LENGTH: 9
<212> TYPE: PRT
<213> ORGANISM: Homo sapiens
<220> FEATURE:
<223> OTHER INFORMATION: Human histone H3 (19-27)

<400> SEQUENCE: 5
```

```
Gln Leu Ala Thr Lys Ala Ala Arg Lys
1               5

<210> SEQ ID NO 6
<211> LENGTH: 4
<212> TYPE: PRT
<213> ORGANISM: Homo sapiens
<220> FEATURE:
<223> OTHER INFORMATION: Human p53 (369-372)

<400> SEQUENCE: 6

Leu Lys Ser Lys
1

<210> SEQ ID NO 7
<211> LENGTH: 6
<212> TYPE: PRT
<213> ORGANISM: Homo sapiens
<220> FEATURE:
<223> OTHER INFORMATION: Human p53 (367-372)

<400> SEQUENCE: 7

Ser His Leu Lys Ser Lys
1               5

<210> SEQ ID NO 8
<211> LENGTH: 4
<212> TYPE: PRT
<213> ORGANISM: Homo sapiens
<220> FEATURE:
<223> OTHER INFORMATION: Human ER alpha (299-302)

<400> SEQUENCE: 8

Lys Arg Ser Lys
1

<210> SEQ ID NO 9
<211> LENGTH: 6
<212> TYPE: PRT
<213> ORGANISM: Homo sapiens
<220> FEATURE:
<223> OTHER INFORMATION: Human ER alpha (297-302)

<400> SEQUENCE: 9

Met Ile Lys Arg Ser Lys
1               5

<210> SEQ ID NO 10
<211> LENGTH: 4
<212> TYPE: PRT
<213> ORGANISM: Homo sapiens
<220> FEATURE:
<223> OTHER INFORMATION: Human AR (630-633)

<400> SEQUENCE: 10

Arg Lys Leu Lys
1

<210> SEQ ID NO 11
<211> LENGTH: 6
<212> TYPE: PRT
<213> ORGANISM: Homo sapiens
<220> FEATURE:
<223> OTHER INFORMATION: Human AR (628-633)

<400> SEQUENCE: 11
```

Gly Ala Arg Lys Leu Lys
1               5

<210> SEQ ID NO 12
<211> LENGTH: 4
<212> TYPE: PRT
<213> ORGANISM: Homo sapiens
<220> FEATURE:
<223> OTHER INFORMATION: Human GR (491-494)

<400> SEQUENCE: 12

Arg Lys Thr Lys
1

<210> SEQ ID NO 13
<211> LENGTH: 6
<212> TYPE: PRT
<213> ORGANISM: Homo sapiens
<220> FEATURE:
<223> OTHER INFORMATION: Human GR (489-494)

<400> SEQUENCE: 13

Glu Ala Arg Lys Thr Lys
1               5

<210> SEQ ID NO 14
<211> LENGTH: 134
<212> TYPE: PRT
<213> ORGANISM: Homo sapiens
<220> FEATURE:
<223> OTHER INFORMATION: Human histone H3

<400> SEQUENCE: 14

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Thr Pro Ser Thr
            20                  25                  30

Cys Gly Val Lys Pro His Arg Tyr Arg Pro Gly Thr Val Ala Leu Arg
        35                  40                  45

Glu Ile Arg Arg Tyr Gln Lys Ser Thr Glu Leu Leu Ile Arg Lys Leu
    50                  55                  60

Pro Phe Gln Arg Leu Val Arg Glu Ile Ala Gln Asp Phe Asn Thr Asp
65                  70                  75                  80

Leu Arg Phe Gln Ser Ala Ala Val Gly Ala Leu Gln Glu Ala Ser Glu
                85                  90                  95

Ala Tyr Leu Val Gly Leu Leu Glu Asp Thr Asn Leu Cys Ala Ile His
            100                 105                 110

Ala Lys Arg Val Thr Ile Met Pro Lys Asp Ile Gln Leu Ala Arg Arg
        115                 120                 125

Ile Arg Gly Glu Arg Ala
    130

<210> SEQ ID NO 15
<211> LENGTH: 129
<212> TYPE: PRT
<213> ORGANISM: Homo sapiens
<220> FEATURE:
<223> OTHER INFORMATION: Human histone H2A

<400> SEQUENCE: 15

Ser Gly Arg Gly Lys Gln Gly Gly Lys Ala Arg Ala Lys Ala Lys Thr
1               5                   10                  15

-continued

```
Arg Ser Ser Arg Ala Gly Leu Gln Phe Pro Val Gly Arg Val His Arg
            20                  25                  30

Leu Leu Arg Lys Gly Asn Tyr Ala Glu Arg Val Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ala Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Lys Val Thr Ile Ala Gln Gly Gly Val Leu Pro Asn Ile Gln
            100                 105                 110

Ala Val Leu Leu Pro Lys Lys Thr Glu Ser His His Lys Ala Lys Gly
        115                 120                 125

Lys

<210> SEQ ID NO 16
<211> LENGTH: 125
<212> TYPE: PRT
<213> ORGANISM: Homo sapiens
<220> FEATURE:
<223> OTHER INFORMATION: Human histone H2B

<400> SEQUENCE: 16

Pro Glu Pro Ser Lys Ser Ala Pro Ala Pro Lys Lys Gly Ser Lys Lys
1               5                   10                  15

Ala Val Thr Lys Ala Gln Lys Lys Asp Gly Lys Arg Lys Arg Ser
            20                  25                  30

Arg Lys Glu Ser Tyr Ser Val Tyr Val Tyr Lys Val Leu Lys Gln Val
        35                  40                  45

His Pro Asp Thr Gly Ile Ser Ser Lys Ala Met Gly Ile Met Asn Ser
    50                  55                  60

Phe Val Asn Asp Ile Phe Glu Arg Ile Ala Gly Glu Ala Ser Arg Leu
65                  70                  75                  80

Ala His Tyr Asn Lys Arg Ser Thr Ile Thr Ser Arg Glu Ile Gln Thr
                85                  90                  95

Ala Val Arg Leu Leu Leu Pro Gly Glu Leu Ala Lys His Ala Val Ser
            100                 105                 110

Glu Gly Thr Lys Ala Val Thr Lys Tyr Thr Ser Ser Lys
        115                 120                 125

<210> SEQ ID NO 17
<211> LENGTH: 102
<212> TYPE: PRT
<213> ORGANISM: Homo sapiens
<220> FEATURE:
<223> OTHER INFORMATION: Human histone H4

<400> SEQUENCE: 17

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
    50                  55                  60
```

```
Val Ile Arg Asp Ala Val Thr Tyr Thr Glu His Ala Lys Arg Lys Thr
 65                  70                  75                  80

Val Thr Ala Met Asp Val Val Tyr Ala Leu Lys Arg Gln Gly Arg Thr
                 85                  90                  95

Leu Tyr Gly Phe Gly Gly
            100

<210> SEQ ID NO 18
<211> LENGTH: 393
<212> TYPE: PRT
<213> ORGANISM: Homo sapiens
<220> FEATURE:
<223> OTHER INFORMATION: Human p53

<400> SEQUENCE: 18

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
                 20                  25                  30

Ser Pro Leu Pro Ser Gln Ala Met Asp Asp Leu Met Leu Ser Pro Asp
             35                  40                  45

Asp Ile Glu Gln Trp Phe Thr Glu Asp Pro Gly Pro Asp Glu Ala Pro
 50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Ala Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

-continued

```
Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 19
<211> LENGTH: 595
<212> TYPE: PRT
<213> ORGANISM: Homo sapiens
<220> FEATURE:
<223> OTHER INFORMATION: Human ER alpha

<400> SEQUENCE: 19

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285
```

```
Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 20
<211> LENGTH: 920
<212> TYPE: PRT
<213> ORGANISM: Homo sapiens
<220> FEATURE:
<223> OTHER INFORMATION: Human AR

<400> SEQUENCE: 20

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45
```

-continued

```
Pro Pro Gly Ala Ser Leu Leu Leu Gln Gln Gln Gln Gln Gln
        50              55                  60
Gln Gln Gln Gln Gln Gln Gln Gln Gln Gln Gln Gln Gln Gln Gln Gln
65                  70                  75                  80
Glu Thr Ser Pro Arg Gln Gln Gln Gln Gln Gly Glu Asp Gly Ser
                85                  90                  95
Pro Gln Ala His Arg Arg Gly Pro Thr Gly Tyr Leu Val Leu Asp Glu
            100                 105                 110
Glu Gln Gln Pro Ser Gln Pro Gln Ser Ala Leu Glu Cys His Pro Glu
                115                 120                 125
Arg Gly Cys Val Pro Glu Pro Gly Ala Ala Val Ala Ala Ser Lys Gly
        130                 135                 140
Leu Pro Gln Gln Leu Pro Ala Pro Pro Asp Glu Asp Asp Ser Ala Ala
145                 150                 155                 160
Pro Ser Thr Leu Ser Leu Leu Gly Pro Thr Phe Pro Gly Leu Ser Ser
                165                 170                 175
Cys Ser Ala Asp Leu Lys Asp Ile Leu Ser Glu Ala Ser Thr Met Gln
            180                 185                 190
Leu Leu Gln Gln Gln Gln Gln Glu Ala Val Ser Glu Gly Ser Ser Ser
        195                 200                 205
Gly Arg Ala Arg Glu Ala Ser Gly Ala Pro Thr Ser Ser Lys Asp Asn
    210                 215                 220
Tyr Leu Gly Gly Thr Ser Thr Ile Ser Asp Asn Ala Lys Glu Leu Cys
225                 230                 235                 240
Lys Ala Val Ser Val Ser Met Gly Leu Gly Val Glu Ala Leu Glu His
                245                 250                 255
Leu Ser Pro Gly Glu Gln Leu Arg Gly Asp Cys Met Tyr Ala Pro Leu
            260                 265                 270
Leu Gly Val Pro Pro Ala Val Arg Pro Thr Pro Cys Ala Pro Leu Ala
        275                 280                 285
Glu Cys Lys Gly Ser Leu Leu Asp Asp Ser Ala Gly Lys Ser Thr Glu
290                 295                 300
Asp Thr Ala Glu Tyr Ser Pro Phe Lys Gly Gly Tyr Thr Lys Gly Leu
305                 310                 315                 320
Glu Gly Glu Ser Leu Gly Cys Ser Gly Ser Ala Ala Ala Gly Ser Ser
                325                 330                 335
Gly Thr Leu Glu Leu Pro Ser Thr Leu Ser Leu Tyr Lys Ser Gly Ala
            340                 345                 350
Leu Asp Glu Ala Ala Ala Tyr Gln Ser Arg Asp Tyr Tyr Asn Phe Pro
        355                 360                 365
Leu Ala Leu Ala Gly Pro Pro Pro Pro Pro Pro Pro His Pro His
370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
            420                 425                 430
Ser Ser Trp His Thr Leu Phe Thr Ala Glu Gly Gln Leu Tyr Gly
        435                 440                 445
Pro Cys Gly Gly Gly Gly Gly Gly Gly Gly Gly Gly
450                 455                 460
Gly Gly Gly Gly Gly Gly Gly Gly Gly Glu Ala Gly Ala Val Ala Pro
```

```
            465                 470                 475                 480
        Tyr Gly Tyr Thr Arg Pro Pro Gln Gly Leu Ala Gly Gln Glu Ser Asp
                        485                 490                 495
        Phe Thr Ala Pro Asp Val Trp Tyr Pro Gly Met Val Ser Arg Val
                        500                 505                 510
        Pro Tyr Pro Ser Pro Thr Cys Val Lys Ser Glu Met Gly Pro Trp Met
                        515                 520                 525
        Asp Ser Tyr Ser Gly Pro Tyr Gly Asp Met Arg Leu Glu Thr Ala Arg
        530                 535                 540
        Asp His Val Leu Pro Ile Asp Tyr Tyr Phe Pro Pro Gln Lys Thr Cys
        545                 550                 555                 560
        Leu Ile Cys Gly Asp Glu Ala Ser Gly Cys His Tyr Gly Ala Leu Thr
                        565                 570                 575
        Cys Gly Ser Cys Lys Val Phe Phe Lys Arg Ala Ala Glu Gly Lys Gln
                        580                 585                 590
        Lys Tyr Leu Cys Ala Ser Arg Asn Asp Cys Thr Ile Asp Lys Phe Arg
                        595                 600                 605
        Arg Lys Asn Cys Pro Ser Cys Arg Leu Arg Lys Cys Tyr Glu Ala Gly
                610                 615                 620
        Met Thr Leu Gly Ala Arg Lys Leu Lys Lys Leu Gly Asn Leu Lys Leu
        625                 630                 635                 640
        Gln Glu Glu Gly Glu Ala Ser Ser Thr Thr Ser Pro Thr Glu Glu Thr
                        645                 650                 655
        Thr Gln Lys Leu Thr Val Ser His Ile Glu Gly Tyr Glu Cys Gln Pro
                        660                 665                 670
        Ile Phe Leu Asn Val Leu Glu Ala Ile Glu Pro Gly Val Val Cys Ala
                        675                 680                 685
        Gly His Asp Asn Asn Gln Pro Asp Ser Phe Ala Ala Leu Leu Ser Ser
                        690                 695                 700
        Leu Asn Glu Leu Gly Glu Arg Gln Leu Val His Val Val Lys Trp Ala
        705                 710                 715                 720
        Lys Ala Leu Pro Gly Phe Arg Asn Leu His Val Asp Asp Gln Met Ala
                        725                 730                 735
        Val Ile Gln Tyr Ser Trp Met Gly Leu Met Val Phe Ala Met Gly Trp
                        740                 745                 750
        Arg Ser Phe Thr Asn Val Asn Ser Arg Met Leu Tyr Phe Ala Pro Asp
                        755                 760                 765
        Leu Val Phe Asn Glu Tyr Arg Met His Lys Ser Arg Met Tyr Ser Gln
        770                 775                 780
        Cys Val Arg Met Arg His Leu Ser Gln Glu Phe Gly Trp Leu Gln Ile
        785                 790                 795                 800
        Thr Pro Gln Glu Phe Leu Cys Met Lys Ala Leu Leu Leu Phe Ser Ile
                        805                 810                 815
        Ile Pro Val Asp Gly Leu Lys Asn Gln Lys Phe Phe Asp Glu Leu Arg
                        820                 825                 830
        Met Asn Tyr Ile Lys Glu Leu Asp Arg Ile Ile Ala Cys Lys Arg Lys
                        835                 840                 845
        Asn Pro Thr Ser Cys Ser Arg Arg Phe Tyr Gln Leu Thr Lys Leu Leu
                        850                 855                 860
        Asp Ser Val Gln Pro Ile Ala Arg Glu Leu His Gln Phe Thr Phe Asp
        865                 870                 875                 880
        Leu Leu Ile Lys Ser His Met Val Ser Val Asp Phe Pro Glu Met Met
                        885                 890                 895
```

Ala Glu Ile Ile Ser Val Gln Val Pro Lys Ile Leu Ser Gly Lys Val
            900                 905                 910
Lys Pro Ile Tyr Phe His Thr Gln
        915                 920

<210> SEQ ID NO 21
<211> LENGTH: 777
<212> TYPE: PRT
<213> ORGANISM: Homo sapiens
<220> FEATURE:
<223> OTHER INFORMATION: Human GR

<400> SEQUENCE: 21

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

```
Asn Thr Ala Ser Leu Ser Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
            370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
            435                 440                 445

Val Glu Gly Gln His Asn Tyr Leu Cys Ala Gly Arg Asn Asp Cys Ile
            450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
            515                 520                 525

Thr Pro Thr Leu Val Ser Leu Leu Glu Val Ile Glu Pro Glu Val Leu
            530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
            595                 600                 605

Gly Trp Arg Ser Tyr Arg Gln Ser Ser Ala Asn Leu Leu Cys Phe Ala
            610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
            675                 680                 685

Ile Arg Met Thr Tyr Ile Lys Glu Leu Gly Lys Ala Ile Val Lys Arg
            690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750
```

```
Leu Ala Glu Ile Ile Thr Asn Gln Ile Pro Lys Tyr Ser Asn Gly Asn
        755                 760                 765
Ile Lys Lys Leu Leu Phe His Gln Lys
    770             775
```

METHOD FOR ASSAYING HISTONE METHYLATION ENZYME ACTIVITY

CROSS-REFERENCE TO RELATED APPLICATIONS

This application is the National Stage of International Application No. PCT/JP2011/002231, filed on 15 Apr. 2011 claiming the priority of JP 2010-096496, filed on 19 Apr. 2010 and JP 2010-202484, filed on 9 Sep. 2010 the content of each of which is incorporated by reference herein.

TECHNICAL FIELD

The present invention relates to a method for measuring histone methyltransferase activity, a method for screening for compounds that inhibit histone methyltransferase activity, a reagent kit for measuring histone methyltransferase activity, and a kit for screening for compounds that inhibit histone methyltransferase activity.

BACKGROUND ART

The chromosomal DNA of a eukaryote forms a complex with protein, and such a complex is called chromatin. More specifically, chromatin involves repeated structures of nucleosomes connected spirally; the nucleosome assumes a conformation in which DNA of 146 base pairs is wrapped 1.75 times around a histone core (a histone octamer) containing 2 molecules each of 4 types of histone proteins: H2A, H2B, H3, and H4. The binding between DNA and histone inhibitorily acts on transcription. It is known that the nucleosome is loosened with histones dissociated in a chromosome containing a gene locus whose transcription is active. Histone consists of a globular carboxyl terminus and a linear amino terminus (histone tail); the lysine residue and asparagine residue of the histone tail are known to undergo various modifications such as acetylation, methylation, phosphorylation, and sumoylation. Outlines of acetylation and methylation among protein post-translational modifications of the lysine residue of histone are shown in FIG. 1. As shown in FIG. 1, the degree of acetylation consists of one level (acetylated lysine ($\epsilon$-N-acetyllysine)) for acetylation, while the degree of methylation consists generally of 3 levels (monomethylated lysine ($\epsilon$-N-methyllysine), dimethylated lysine ($\epsilon$-N,N-dimethyllysine), and trimethylated lysine ($\epsilon$-N,N,N-trimethyllysine))) for methylation.

The methylation modification is known to cause transcriptional control, silencing, chromatin condensation, and the like. The methylation of histone is induced by histone methyltransferase (HMT). FIG. 2 shows the names of human histone methyltransferases heretofore known, the lysine sites at which these enzymes are methylated (lysine sites), and the influence of the methylation of the lysine sites on transcription (transcriptional enhancement or transcriptional repression). The histone methylation is known to be associated with various diseases. For example, Non-Patent Document 1 describes that various histone methyltransferases such as SUV39H1, EZH2, MLL, NSD1, and RIZ are responsible for tumor development. Non-Patent Documents 2 and 3 also describe that the methylation of histone H3K9 and histone H3K27 is observed together with increased DNA methylation and decreased histone acetylation in the promoter region of a cancer suppressor gene whose expression is suppressed in cancer cells. In addition, Non-Patent Document 4 describes that increased methylation of histone H4K20 is observed in common to many cancers. Non-Patent Document 5 also describes that the formation of a heterochromatin induced by the methylation of histone is involved in neurodegenerative diseases such as myotonic dystrophy and Friedreich motor ataxia. Non-Patent Document 6 also describes that iPS cells were induced by adding BayK8644 as an agonist of L-type calcium channels and BIX-01294 as an inhibitor for the histone methyltransferase G9a to Oct4/Klf2 and gene-introduced mouse embryo fibroblasts.

Thus, a histone methyltransferase inhibitor is expected as a therapeutic agent for diseases such as cancer and neurodegenerative disease and to be applied to regenerative medicine using iPS cells. Accordingly, screening for histone methyltransferases is attempted. For example, Non-Patent Document 7 describes a method which involves mixing [methyl-3H]-SAM as S-adenosylmethionine (S-(5'-adenosyl)-L-methionine: SAM) whose methyl group is labeled with tritium, a peptide consisting an amino acid sequence of amino acid 1 to 19 of histone H3 (histone H3 (1-19) peptide), and a histone methyltransferase for reaction, followed by measuring the radioactivity of the histone H3 (1-19) peptide to measure the amount of the methyl group transferred to lysine to thereby measure the histone methylation activity of the histone methyltransferase (so-called RI method) (FIG. 3). Non-Patent Document 8 also describes a method for screening for histone methyltransferase inhibitors by an Elisa method (FIG. 4). However, the RI method has had problems of being limited in safety because of using the radioisotope, being complicated because of requiring relatively many experimental procedures including the adsorption of a reaction product to filter paper and the washing of the filter paper, and the like (FIG. 5). As shown in FIG. 5, the Elisa method has had problems of an extremely large number of experimental procedures such as a washing procedure and a large amount of time required. Under such circumstances, there has been a need for an evaluation system for histone methylation activity, wherein the system has no problem with safety and is simple in the experimental procedures and short in time required.

A known simple method for measuring histone deacetylase activity includes a method using a substrate peptide represented by X-X-Lys(Ac)-(dye) (that is, a substrate peptide represented by X-X-(Ac)Lys-(dye) in Patent Document 1), (wherein X represents any amino acid residue; Lys(Ac) represents a lysine residue whose $\epsilon$ amino group (an amino group at the $\epsilon$ position) is acetylated; and (dye) represents a dye label bound to the lysine residue) (see Patent Document 1). This method uses the property that the cleavage activity of a certain peptidase remains lowered in a state where the substrate peptide remains acetylated, while the cleavage activity of the peptidase is increased when the substrate peptide is deacetylated.

With regard to methylation at the $\epsilon$ position of lysine, Non-Patent Documents 9 and 10 describe that methylation at the $\epsilon$ position of lysine residue of a peptide renders the peptide less susceptible to decomposition by trypsin than no such methylation. However, it has been uncertain whether the methylation at the $\epsilon$ position of lysine can actually be used for a method for measuring histone methyltransferase activity, for example, because it consists of 3 steps (monomethylation, dimethylation, and trimethylation), unlike the acetylation, and decreases the cleavage activity of a certain peptidase as the reaction proceeds, contrary to the deacetylation in the above-described Patent Document 1.

PRIOR ART DOCUMENTS

Patent Documents

Patent Document 1
Japanese Patent No. 4267043

Non-Patent Documents

Non-Patent Document 1
TRENDS in Biochemical Sciences, 27: 396-402, 2002.
Non-Patent Document 2
Nature Review Cancer, 6: 107-116, 2006.
Non-Patent Document 3
Nature Review Drug Discovery, 5: 37-50, 2006.
Non-Patent Document 4
Nature Genetics, 37: 391-400, 2005.
Non-Patent Document 5
Nature, 422: 909-913, 2003.
Non-Patent Document 6
Cell Stem Cell, 3: 568-574, 2008.
Non-Patent Document 7
Nature Chemical Biology, 1: 143-145, 2005.
Non-Patent Document 8
Molecular Cell, 25: 473-481, 2007.
Non-Patent Document 9
Biochim Biophys Acta, Vol. 581 No. 2: 360-362, 1979.
Non-Patent Document 10
J. Biol Chem, Vol. 258 No. 3: 1844-1850, 1983.

SUMMARY OF THE INVENTION

Object to be Solved by the Invention

An object of the present invention is to provide a method for measuring histone methyltransferase activity, a method for screening for compounds that inhibit histone methyltransferase activity, a reagent kit for measuring histone methyltransferase activity, and a kit for screening for compounds that inhibit histone methyltransferase activity.

Means to Solve the Object

To solve the above-described problems, the present inventors attempted to construct an evaluation system or the like in which the methylation of the ε amino group of the lysine residue increases the intensity of detection of the dye, but could not construct a simple and sensitive evaluation system. However, as a result of further intensive studies, the present inventors have found that the use of a substrate compound represented by the above-described general formula (I) can actually sensitively measure histone methyltransferase activity even in an evaluation system in which the methylation of the ε amino group of the lysine residue decreases the intensity of detection of the dye, thereby accomplishing the present invention. As a result of further advancing studies, the present inventors have found that a simple and sensitive evaluation system can be constructed in which the methylation of the ε amino group of the lysine residue increases the intensity of detection of the dye by use of suitable excitation and fluorescence wavelengths, thereby accomplishing the present invention.

Thus, the present invention relates to (1) a method for measuring histone methyltransferase activity in a sample, comprising the steps of:

(a) providing a substrate compound represented by the following general formula (I):

$$R_1-X-K-R_2 \tag{I}$$

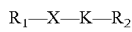

or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue),
wherein the cleavage of the amide bond by peptidase changes the fluorescence property or chromogenic property of the dye label and the methylation of the ε amino group of the lysine residue by the histone methyltransferase decreases susceptibility to peptidase;

(b) contacting the substrate compound represented by the general formula (I) or a salt thereof with a sample under conditions required for methylation reaction by the histone methyltransferase;

(c) exposing the substrate compound or a salt thereof to peptidase after the step (b);

(d) measuring the degree of the change of the fluorescence property or chromogenic property of the dye label after the step (c) to calculate the degree of the increase of the methylation level of the substrate compound or a salt thereof, based on the degree of the decrease of the cleavage activity of the peptidase that uses the substrate compound or a salt thereof as a substrate; and (e) evaluating the degree of the increase of the methylation level in the step (d) as the degree of histone methyltransferase activity in the sample;

(2) the method according to (1) above, wherein the measurement of the degree of the change of the fluorescence property or chromogenic property of the dye label in the step (d) is performed by:

measuring the dye label whose fluorescence property or chromogenic property has been changed by the cleavage of the amide bond in the substrate compound or a salt thereof by peptidase; or measuring the dye label in which the amide bond has not been cleaved by peptidase because of the methylation of the ε amino group of a lysine residue in the substrate compound or a salt thereof;

(3) a method for screening for compounds that inhibit histone methyltransferase activity, comprising the steps of:

(a) providing a substrate compound represented by the following general formula (I):

$$R_1-X-K-R_2 \tag{I}$$

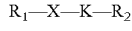

or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue),
wherein the cleavage of the amide bond by peptidase changes the fluorescence property or chromogenic property of the dye label, and the methylation of the ε amino group of the lysine residue by the histone methyltransferase decreases susceptibility to peptidase;

(b) contacting the substrate compound represented by the general formula (I) or a salt thereof with the histone methyltransferase in the presence of a test compound under conditions required for methylation reaction by histone methyltransferase;

(c) exposing the substrate compound or a salt thereof to peptidase after the step (b);

(d) measuring the degree of the change of the fluorescence property or chromogenic property of the dye label after the step (c) to calculate the degree of the increase of the methylation level of the substrate compound or a salt thereof, based on the degree of the decrease of the cleavage activity of the peptidase that uses the substrate compound or a salt thereof as a substrate; and (e) selecting a test compound for which the degree of the increase of the methylation level of the substrate compound or a salt thereof in the step (d) is low compared to the degree of the increase of the methylation level of the substrate compound or a salt thereof in the absence of the test compound; and (4) the method according to any one of (1) to (3) above, wherein the peptidase is at least one peptidase selected from the group consisting of lysyl endopeptidase, endoproteinase Lys-C, plasmin, calpain, and trypsin.

The present invention also relates to (5) a substrate compound represented by the following general formula (I):

$$R_1-X-K-R_2 \quad (I)$$

or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue), wherein the cleavage of the amide bond by peptidase changes the fluorescence property or chromogenic property of the dye label, and the methylation of the ε amino group of the lysine residue by the histone methyltransferase decreases susceptibility to peptidase; and (6) the substrate compound or a salt thereof according to (5) above, wherein the histone methyltransferase is a histone methyltransferase having a substrate specificity depending on a peptide sequence consisting of X—K and the sequence of the peptide sequence consisting of X—K in the substrate compound or a salt thereof is a sequence exhibiting a substrate specificity for the histone methyltransferase.

In addition, the present invention relates to (7) a reagent kit for measuring histone methyltransferase activity, comprising the following elements (a) and (b):

(a) a substrate compound for measuring histone methyltransferase activity represented by the following general formula (I):

$$R_1-X-K-R_2 \quad (I)$$

or a salt thereof, (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue), wherein the cleavage of the amide bond by peptidase changes the fluorescence property or chromogenic property of the dye label, and the methylation of the ε amino group of the lysine residue by the histone methyltransferase decreases susceptibility to peptidase; and (b) a peptidase capable of cleaving a substrate compound represented by the general formula (I) or a salt thereof, wherein the peptidase is a peptidase whose cleavage activity decreases as the methylation level of the substrate compound or a salt thereof increases;

(8) the reagent kit according to (7) above, wherein the peptidase is at least one peptidase selected from the group consisting of lysyl endopeptidase, endoproteinase Lys-C, plasmin, calpain, and trypsin; and (9) a kit for screening for compounds that inhibit histone methyltransferase activity, comprising the reagent kit according to (7) or (8) above and histone methyltransferase.

Effect of the Invention

The present invention simply and sensitively enables the measurement of histone methyltransferase activity and the screening for compounds that inhibit histone methyltransferase activity.

BRIEF DESCRIPTION OF DRAWINGS

FIG. 1 is a diagram showing outlines of the acetylation (the upper of FIG. 1) and methylation (the lower of FIG. 1) of the lysine residue of histone.

FIG. 2 is a table showing the names of human histone methyltransferases, the lysine sites at which these enzymes are methylated, and the influence of the methylation of the lysine sites.

FIG. 5 is a diagram showing problems with an RI method and an Elisa method as conventional methods.

FIG. 13 is a diagram showing the amino acid sequence of an X peptide of each peptidyl substrate compound in which X in the substrate compound of the present invention indicates one or more amino acid residues (peptide), and the like.

FIG. 14 is a pair of graphs showing the results of an assay for measuring histone methyltransferase activity using a peptidyl MCA. The vertical axis represents the proportion (%) of an unmethylated peptidyl MCA, and the horizontal axis represents the concentration (μg/μL) of GST-mG9a or His-Set9. The left panel of FIG. 14 shows the results for the use of G9a as a histone methyltransferase. The right panel of FIG. 14 shows the results for the use of Set9 as a histone methyltransferase.

FIG. 15 is a diagram showing the amino acid sequence of an X peptide of each peptidyl substrate compound in which X in the substrate compound of the present invention indicates one or more amino acid residues (peptide), and the like.

FIG. 16 is a pair of graphs showing the results of an assay for measuring histone methyltransferase activity using a peptidyl MCA. The vertical axis represents the proportion (%) of an unmethylated peptidyl MCA, and the horizontal axis represents the concentration (μg/μL) of GST-mG9a or His-Set9. The left panel of FIG. 16 shows the results for the use of G9a as a histone methyltransferase. The right panel of FIG. 16 shows the results for the use of Set9 as a histone methyltransferase.

FIG. 17 is a drawing showing the results of western blot for evaluating an activity of a histone methyltransferase activity inhibitor.

MODE OF CARRYING OUT THE INVENTION

1. "Substance compound and Salt Thereof" of the Present Invention

Figure 3:
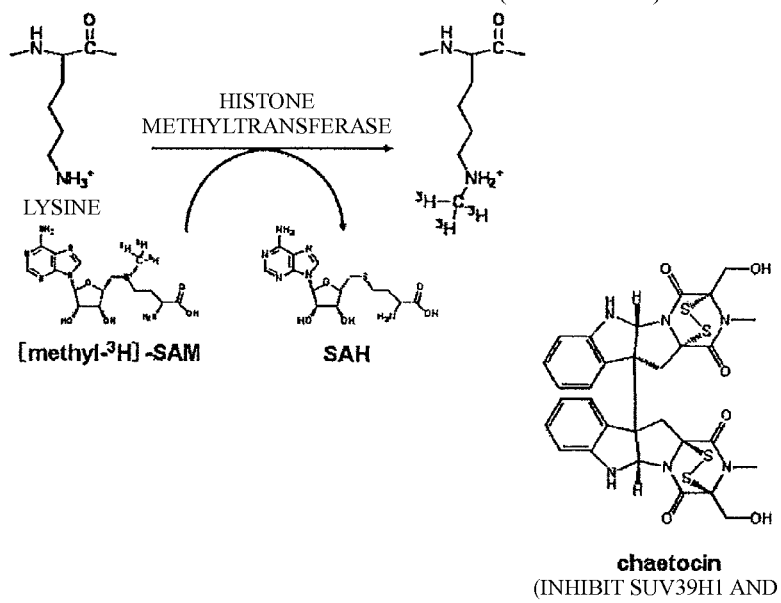
FIG. 3 is a diagram showing an outline of a conventional method for measuring histone methylation activity (RI method).
Figure 4:
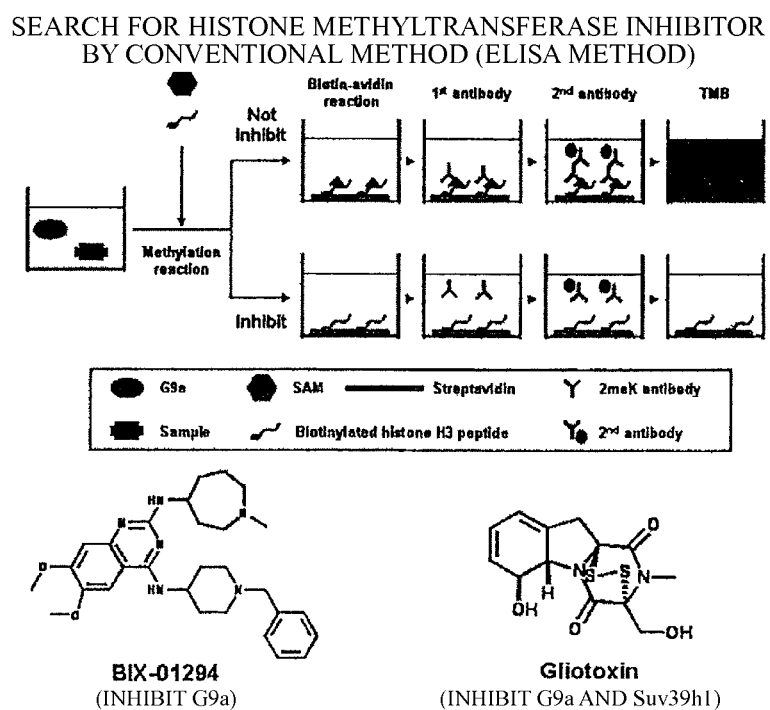
FIG. 4 is a diagram showing an outline of a conventional method for measuring histone methylation activity (Elisa method).
Figure 6:
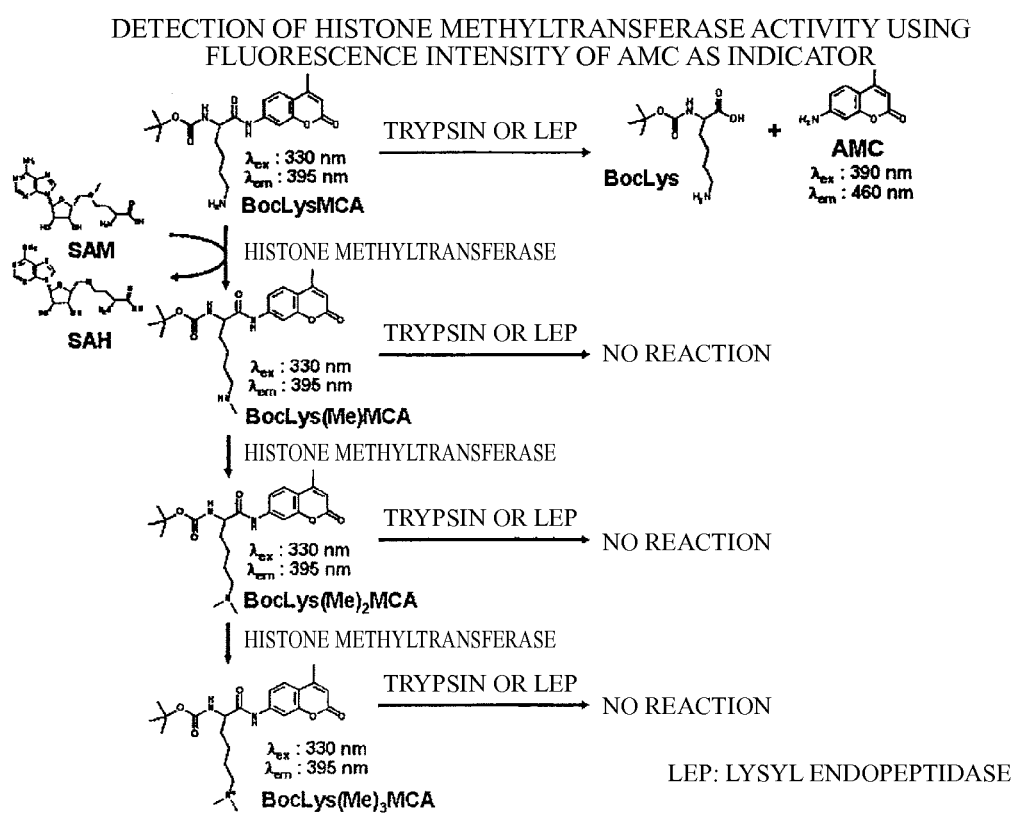
FIG. 6 is a diagram showing an outline of a method for measuring histone methyltransferase activity when BocLysMCA is used.

The substrate compound of the present invention or a salt thereof (hereinafter, also simply referred to as "the substrate compound or the like of the present invention") is not particularly limited provided that they are each a substrate compound for measuring histone methyltransferase activity represented by the above general formula (I), or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue), wherein the cleavage of the amide bond by peptidase changes the fluorescence property or chromogenic property of the dye label, and the methylation of the ε amino group of the lysine residue by the histone methyltransferase decreases susceptibility to peptidase. The substrate compound or the like of the present invention and a sample can be contacted with each other under conditions required for methylation reaction by histone methyltransferase and then exposed to peptidase, followed by measuring the degree of the change of the fluorescence property or chromogenic property of the dye label to calculate the degree of the increase of the methylation level of the substrate compound or the like, based on the degree of the decrease of the cleavage activity of the peptidase using the substrate compound or a salt thereof as a substrate to evaluate the degree of the increase of the methylation level as the degree of histone methyltransferase activity in a sample. In this way, the substrate compound or the like of the present invention can be used to highly simply and sensitively measure histone methyltransferase activity in a sample. The object to be measured in measuring the degree of the change of the fluorescence property or chromogenic property of the dye label may be a dye label whose fluorescence property or chromogenic property has been changed by the cleavage of the amide bond in the substrate compound or the like by peptidase (hereinafter, also indicated as "dye label A") or a dye label in which the amide bond has not been cleaved by peptidase because of the methylation of the ε amino group of the lysine residue in the substrate compound or the like (hereinafter, also indicated as "dye label B"). An outline of a method for measuring histone methyltransferase activity when BocLysMCA is used as the substrate compound or the like of the present invention is shown in FIG. 6. As shown in FIG. 6, the unmethylation of the substrate compound or the like of the present invention results in the cleavage of its amide bond by peptidase to provide a dye label (AMC) whose fluorescence property has been changed, while the methylation of the ε amino group of the lysine residue in the substrate compound or the like does not result in the cleavage of the amide bond by peptidase to not so change the fluorescence property of a dye label (MCA group). When dye label A such as AMC is measured, the histone methyltransferase activity can be measured from the amount of decrease of the dye label A, and when dye label B such as MCA group is measured, the histone methyltransferase activity can be measured from the amount of increase of the dye label B.

The above-described $R_1$ may be anything which is a hydrogen atom or a protecting group for an amino terminus, and specific examples of the amino-terminus protecting group can include —HCO, —CH$_3$CO, —CH$_3$CH$_2$CO, a Boc(t-butyloxycarbonyl) group, a benzyl group, a propionyl group, and a tosyl group. The above-described $R_2$ is not particularly limited provided that it is a dye label linked via an amide bond to the carbonyl terminus of the lysine residue (K) in the general formula (I), wherein the cleavage of the amide bond (the amide bond between the lysine residue and $R_2$) by peptidase changes the fluorescence property or chromogenic property of the dye label. Specific examples of the group which is a dye label linked via an amide bond to the carbonyl terminus of the lysine residue (K) and whose fluorescence property is changed by the cleavage of the amide bond can include an MCA (4-methyl-coumaryl-7-amide) group, an ANS (2-aminonaphthalene-6-sulfonic acid) group, a CMCA (7-amino-4-chloromethylcoumarin) group, an FMCA (7-amino-4-trifluoromethylcoumarin) group, an AMP (2-amino-7-methylpurine-6-thiol) group, an R110 (rhodamine 110) group, and an R110 monoamide (rhodamine 110 monoamide) group, wherein the MCA group, the ANS group, the CMCA group, the FMCA group, the AMP group, the R110 group, and the R110 monoamide group mean substituents shown in the following [Formula 5]. The peptide group in the R110 monoamide group shown in [Formula 5] is not particularly limited and may be any peptide group.

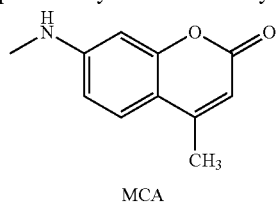

MCA

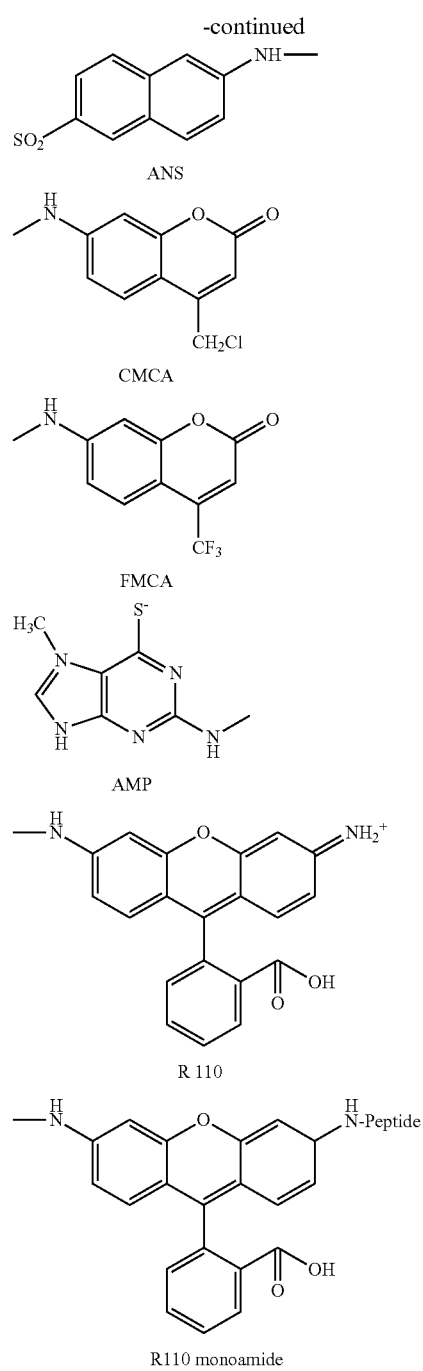

Specific examples of the group which is a dye label linked via an amide bond to the carbonyl terminus of the lysine residue (K) and whose chromogenic property is changed by the cleavage of the amide bond can include a pNA (p-nitroaniline) group and a βAN (β-amino naphthalene) group; for convenience, the βAN group includes a secondary reaction product between βAN and Fast Garnet GBC, Fast Blue, or the like, wherein the pNA group, the βAN group, Fast Garnet GBC, and Fast Blue mean substituents or the like shown in the following [Formula 6].

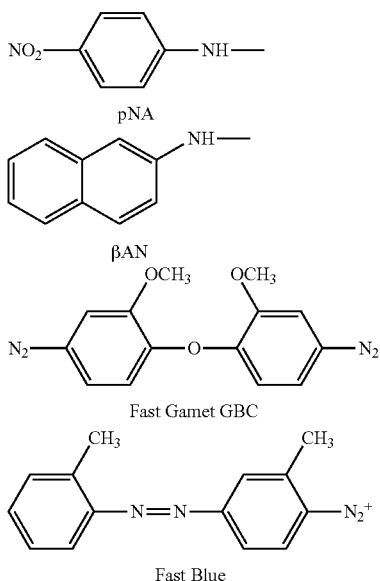

pNA

βAN

Fast Garnet GBC

Fast Blue

The presence or amount of change of the fluorescence property can be detected and quantified using a fluorescence intensity-measuring device or the like, and the presence or amount of change of the chromogenic property can be detected and quantified using a spectrophotometer or the like. In this regard, it is preferable to analyze the absorption wavelengths and fluorescence wavelengths of the dye label A and the dye label B to select the excitation wavelength and fluorescence wavelength at which any of them can be specifically detected and quantified. When the MCA group is used as a dye label in the substrate compound or the like of the present invention, a wavelength exciting AMC without exciting the MCA group (for example, 360 nm to 400 nm, preferably 385 nm to 395 nm, particularly preferably 390 nm) is preferably irradiated to detect and measure a fluorescence wavelength (for example, 400 nm to 500 nm, preferably 440 nm to 480 nm, particularly preferably 460 nm) emitted by AMC for the specific measurement of AMC, and a wavelength exciting the MCA group (for example, 260 nm to 350 nm, preferably 300 nm to 340 nm, particularly preferably 330 nm) is preferably irradiated to detect and measure a wavelength (for example, 350 nm to 385 nm, preferably 365 nm to 385 nm, particularly preferably 380 nm) emitted not by AMC but by the MCA group for the specific measurement of the MCA group. The use of these wavelengths enables the simple and sensitive measurement of histone methyltransferase activity.

In the general formula (I), X represents a peptide consisting of 0 or 1 or more, preferably 1 to 30, more preferably 1 to 10 amino acid residues and K represents a lysine residue. X—K in the general formula (I) is a peptide derived from histone H3, histone H2A, histone H2B, histone H4, p53, estrogen receptor a (ERα), androgen receptor (AR), glucocorticoid receptor (GR), or the like. Preferred examples of the X—K derived from histone H3 can include a peptide consisting of the amino acid residues of amino acid 1 to 4 of human histone H3 (ARTK; SEQ ID NO: 1), a peptide consisting of the amino acid residues of amino acid 5 to 9 of human histone H3 (QTARK; SEQ ID NO: 2), a peptide consisting of the amino acid residues of amino acid 1 to 9 of human histone H3 (ARTKQTARK; SEQ ID NO: 3), a peptide consisting of the amino acid residues of amino acid 7 to 9 or 25 to 27 of human histone H3 (ARK), a peptide consisting of the amino acid residues of amino acid 23 to 27 of human histone H3 (KAARK; SEQ ID NO: 4), and a peptide consisting of the amino acid residues of amino acid 19 to 27 of human histone H3 (QLATKAARK; SEQ ID NO: 5). Preferred examples of the X—K derived from p53 can include a peptide consisting of the amino acid residues of amino acid of 369 to 372 of human p53 (LKSK; SEQ ID NO: 6), and a peptide consisting of the amino acid residues of amino acid of 367 to 372 of human p53 (SHLKSK; SEQ ID NO: 7). Preferred examples of the X—K derived from ERα can include a peptide consisting of the amino acid residues of amino acid of 299 to 302 of human ERα (KRSK; SEQ ID NO: 8) and a peptide consisting of the amino acid residues of amino acid of 297 to 302 of human ERα (MIKRSK; SEQ ID NO: 9). Preferred examples of the X—K derived from AR can include a peptide consisting of the amino acid residues of amino acid of 630 to 633 of human AR (RKLK; SEQ ID NO: 10) and a peptide consisting of the amino acid residues of amino acid of 628 to 633 of human AR (GARKLK; SEQ ID NO: 11). Preferred examples of the X—K derived from GR can include a peptide consisting of the amino acid residues of amino acid of 491 to 494 of human GR (RKTK; SEQ ID NO: 12) and a peptide consisting of the amino acid residues of amino acid of 489 to 494 of human GR (EARKTK; SEQ ID NO: 13). The amino acid sequence of human histone H3 is shown in SEQ ID NO: 14; the amino acid sequence of human histone H2A is shown in SEQ ID NO: 15; the amino acid sequence of human histone H2B is shown in SEQ ID NO: 16; the amino acid sequence of human histone H4 is shown in SEQ ID NO: 17; the amino acid sequence of human p53 is shown in SEQ ID NO: 18; the amino acid sequence of human ERα is shown in SEQ ID NO: 19; the amino acid sequence of human histone AR is shown in SEQ ID NO: 20; and the amino acid sequence of human GR is shown in SEQ ID NO: 21.

The salt of the substrate compound of the present invention may be any salt provided that it is a salt of the compound giving a measured value comparable to the measured value obtained by measuring histone methyltransferase activity using the substrate compound of the present invention as a substrate for measuring the histone methyltransferase activity; specific examples thereof can include salts with bases or acid addition salts including salts with inorganic bases (for example, alkali metal salts such as a sodium salt and a potassium salt, alkali earth metal salts such as a calcium salt and a magnesium salt, and ammonium salts), salts with organic bases (for example, triethylamine salts and diisopropylethylamine salts), inorganic acid addition salts (for example, hydrochlorides, hydrobromates, sulfates, and phosphates), organic carboxylic acid or sulfonic acid addition salts (for example, formates, acetates, trifluoroacetates, benzenesulfonates, and toluenesulfonates).

Among substrate compounds of the present invention or the like, particularly preferred specific examples thereof can include Boc-K-MCA (BocLysMCA), Ac-ARTK-MCA (Ac-histone H3 (1-4)-MCA), Ac-QTARK-MCA (Ac-histone H3 (5-9)-MCA), Ac-ARTKQTARK-MCA (Ac-histone H3 (1-9)-MCA), Ac-ARK-MCA (Ac-histone H3 (7-9/25-27)-MCA), Ac-KAARK-MCA (Ac-histone H3 (23-27)-MCA), Ac-QLATKAARK-MCA (Ac-histone H3 (19-27)-MCA), Ac-LKSK-MCA (Ac-p53 (369-372)-MCA), Ac-SHLKSK-MCA (Ac-p53 (367-372)-MCA), Ac-KRSK-MCA (Ac-ERα (299-302)-MCA), Ac-MIKRSK-MCA (Ac-ERα (297-302)-MCA), Ac-RKLK-MCA (Ac-AR (630-633)-MCA), Ac-GARKLK-MCA (Ac-AR (628-633)-MCA) Ac-RKTK-MCA (Ac-GR(491-494)-MCA), and Ac-EARKTK-MCA (Ac-GR (489-494)-MCA).

The substrate compound or the like of the present invention is decreased in susceptibility to peptidase when the ε amino group of the lysine residue thereof is methylated by histone methyltransferase. Preferred examples of the degree of the decrease of susceptibility can include, for example, when the amount of the dye label A (the signal intensity of the dye label A, preferably the fluorescence intensity, more preferably the fluorescence intensity of AMC) is compared between the substrate compound or the like of the present invention in which one hydrogen atom of the ε amino group of the lysine residue of the substrate compound or the like of the present invention is methylated (Me) and the substrate compound or the like of the present invention in the following mixing assay, a percentage of the amount of the dye label A of the substrate compound or the like of the present invention (Me) relative to the amount of the dye label A of the substrate compound or the like of the present invention of 30% or less, preferably 20% or less, more preferably 10% or less, more preferably 5% or less, more preferably 3% or less, more preferably 1% or less. Thus, the use of the substrate compound or the like of the present invention exhibiting the significant degree of decrease enables the highly sensitive measurement of histone methyltransferase activity.

(Mixing Assay)

Distilled water is added to 10 μL of 2×HMT buffer (100 mM Tris-HCl (pH 8.5), 20 mM $MgCl_2$, 40 mM KCl, 20 mM 2-mercaptoethanol, 500 mM sucrose) and 1 μL of a solution of the substrate compound or the like of the present invention to adjust the total volume to 20 μL. To the resultant solution is added 30 μL of a peptidase solution (preferably 20 mg/mL trypsin or 20 mAU/mL lysyl endopeptidase), which is then mixed and incubated at 37° C. for 15 minutes. Then, the amount of the dye label A in the solution is measured. In the same manner, the amount of the dye label A of the substrate compound or the like of the present invention (Me) is measured. When the amount of the dye label A is represented by the fluorescence intensity of AMC, it is preferable to measure the fluorescence intensity at an excitation wavelength (λex) of 390 nm and a fluorescence wavelength (λem) of 460 nm. The wavelength is a wavelength for detecting AMC (7-amino-4-methylcoumarin) released by the cleavage of the amide bond between Lys and MCA of the substrate compound or the like of the present invention.

As used herein, the "histone methyltransferase" is not particularly limited provided that it is an enzyme capable of methylating the ε amino group of the lysine residue of histone; however, preferred examples thereof can include SET1, MLL, SET9, SMYD3, Meisetz, SUV39H1, G9a, GLP, ESET/SETDB1, RIZ, MES-2, EZH2, NSD1, SMYD2, DOT1L, SUV4-20H, NSD1, and SETS/PR-SET7, and especially preferred examples thereof can include SET9 and G9a. SET1, MLL, SET9, SMYD3, and Meisetz are each an enzyme methylating the lysine residue of amino acid 4 of histone H3 (histone H3K4), wherein they contribute to transcriptional enhancement by the methylation. SUV39H1, G9a, GLP, ESET/SETDB1, and RIZ are each an enzyme methylating the lysine residue of amino acid 9 of histone H3 (histone H3K9), wherein they contribute to transcriptional repression by the methylation. MES-2, EZH2, and G9a are each an enzyme methylating the lysine residue of amino acid 27 of histone H3 (histone H3K27), wherein they contribute to transcriptional repression by the methylation. NSD1 and SMYD2 are each an enzyme methylating the lysine residue of amino acid 36 of histone H3 (histone H3K36), wherein they contribute to transcriptional enhancement by the methylation. DOT1L is an enzyme methylating the lysine residue of amino acid 79 of histone H3 (histone H3K79), wherein they contribute to transcriptional enhancement by the methylation. SUV4-20H, NSD1, and SET8/PR-SET7 are each an enzyme methylating the lysine residue of amino acid 20 of histone H4 (histone H4K20), wherein they contribute to transcriptional repression by the methylation. The enzyme called SETS is the same enzyme as the enzyme called SET7; thus, they are sometimes indicated as SET7/9 in the description of the present invention.

Examples of the histone methyltransferase cleaving the amide bond between K and $R_2$ in the substrate compound or the like of the present invention can include a histone methyltransferase having substrate specificity depending on the sequence of a peptide consisting of X—K. Such a histone methyltransferase methylates only a substrate compound or the like of the present invention having a peptide consisting of X—K specific for the enzyme; thus, the reaction thereof with substrate compounds or the like of the present invention having various X-peptide sequences can be determined to examine the substrate specificity of the histone methyltransferase. The reaction of a substrate compound or the like of the present invention in which X is a peptide having a predetermined sequence with various histone methyltransferases can be determined to examine a histone methyltransferase specific for the substrate compound or the like. The histone methyltransferase for the substrate compound or the like of the present invention is a histone methyltransferase having substrate specificity depending on a peptide consisting of X—K, and the sequence of the peptide consisting of X—K in the substrate compound or the like of the present invention can be preferably exemplified by the substrate compound or the like of the present invention as a sequence exhibiting substrate specificity for the histone methyltransferase.

The substrate compound or the like of the present invention can be synthesized by a known method. For example, $R_1$—X—OH can be reacted with an acidic salt of K—$R_2$ to synthesize a substrate compound represented by the general formula (I).

For the purpose of the present invention, the "peptide" means a compound in which 2 or more amino acids are bonded to each other by peptide bond, and the chain length is not particularly limited. For the purpose of the present invention, the "methyltransferase" means an enzyme catalyzing the reaction of transferring a methyl group from a substance having a methyl group as a part of the structure thereof (for example, S-adenosylmethionine: SAM) to the peptide. For the purpose of the present invention, the "peptidase" means an enzyme acting on a group of peptides including a protein to hydrolyze peptide bonds, wherein the enzyme is decreased in cleavage activity on the substrate compound or the like by the methylation of the ε amino group of the lysine residue of substrate compound or the like of the present invention. Thus, all of the so called "proteolytic enzyme", "protease", "proteinase", "peptidehydrolase", and the like fall within "peptidase" for the purpose of the present invention. Specific examples of the "peptidase" for the purpose of the present invention can include lysyl endopeptidase, endoproteinase Lys-C, plasmin, calpain, and trypsin; among others, preferred examples thereof can include lysyl endopeptidase and trypsin. For the purpose of the present invention, the "peptide-cleaving activity" means an activity hydrolyzing a peptide bond in a peptide serving as a substrate.

2. "Reagent Kit for Measuring Histone Methyltransferase Activity" of the Present Invention The reagent kit for measuring histone methyltransferase activity according to the present invention is not particularly limited provided that it is a kit comprising the following elements (a) and (b):

(a) the substrate compound or the like of the present invention; and (b) a peptidase cleaving the substrate compound or the like of the present invention, wherein the peptidase decreases in cleavage activity as the methylation level of the substrate compound or the like of the present invention increases.

The reagent kit for measuring histone methyltransferase activity according to the present invention can be used by the same method as a "method for measuring histone methyltransferase activity in a sample" to be described later.

3. "Kit for Screening for Compounds Inhibiting Histone Methyltransferase Activity" of the Present Invention The kit for screening for compounds inhibiting histone methyltransferase activity according to the present invention is not particularly limited provided that it is a kit comprising the reagent kit for measuring histone methyltransferase activity according to the present invention and a histone methyltransferase. The histone methyltransferase contained in the kit is a histone methyltransferase having substrate specificity depending on the sequence of a peptide consisting of X—K in the substrate compound or the like of the present invention, and the sequence of the peptide consisting of X—K in the substrate compound or the like of the present invention can be preferably exemplified by a sequence exhibiting substrate specificity for the histone methyltransferase.

The kit for screening for compounds inhibiting histone methyltransferase activity according to the present invention can be used by the same method as a "method for screening for compounds inhibiting histone methyltransferase activity" to be described later.

4. "Method for measuring Histone Methyltransferase Activity in Sample" of the Present Invention The method for measuring histone methyltransferase activity in a sample according to the present invention is not particularly limited provided that it comprises the following steps of:

(a) providing the substrate compound or the like of the present invention;

(b) contacting the substrate compound or the like of the present invention with a sample under conditions required for methylation reaction by histone methyltransferase;

(c) exposing the substrate compound or the like of the present invention to peptidase after the step (b);

(d) measuring the degree of the change of the fluorescence property or chromogenic property of the dye label after the step (c) to calculate the degree of the increase of the methylation level of the substrate compound or the like of the present invention, based on the degree of the decrease of the cleavage activity of the peptidase that uses the substrate compound or the like of the present invention as a substrate; and (e) evaluating the degree of the increase of the methylation level in the step (d) as the degree of histone methyltransferase activity in the sample.

The method can highly simply and sensitively measure histone methyltransferase activity in a sample. The step (a) is not particularly limited provided that it is a step of providing the substrate compound or the like of the present invention, and includes a step of preparing the substrate compound or the like of the present invention. The step (b) is not particularly limited provided that it is a step of contacting the substrate compound or the like of the present invention with a sample under conditions required for methylation reaction by histone methyltransferase; however, preferred examples thereof can include contacting the substrate compound or the like of the present invention with a sample in a solution meeting conditions required for methylation reaction by histone methyltransferase. Such conditions can be selected as needed and include conditions of containing a methyl group donor such as S-adenosylmethionine (SAM) and such conditions that the histone methyltransferase can exert histone methyltransferase activity. Preferred examples of the step (b) can include adding distilled water to 10 µL of 2×HMT buffer (100 mM Tris-HCl (pH 8.5), 20 mM $MgCl_2$, 40 mM KCl, 20 mM 2-mercaptoethanol, 500 mM sucrose), 2 µL of a BSA solution (30 µg/mL), and a predetermined concentration of a histone methyltransferase solution to adjust the total volume to 16 µL, incubating the resultant solution at room temperature for 1 hour, and then adding 2 µL of SAM and 2 µL of the substrate compound or the like of the present invention thereto, followed by incubation at 37° C. for 1 hour.

The step (c) is not particularly limited provided that it is a step of exposing the substrate compound or the like of the present invention to peptidase after the step (b); preferred examples thereof can include a step of adding a peptidase solution, followed by incubation at 37° C. for 15 minutes.

The step (d) is not particularly limited provided that it is a step of measuring the degree of the change of the fluorescence property or chromogenic property of the dye label capable of occurring by the cleavage of the amide bond between K and $R_2$ of the substrate compound or the like of the present invention after the step (c) to calculate the degree of the increase of the methylation level of the substrate compound or the like of the present invention, based on the degree of the decrease of the cleavage activity of the peptidase using the substrate compound or the like of the present invention as a substrate. A method for measuring the degree of the change of the fluorescence property or chromogenic property of the dye label can be properly selected depending on the type of the changing property of the dye label. For example, when the changing property of the dye label is a fluorescence property, a fluorescence intensity-measuring device or the like can be used to detect the presence of change of the fluorescence property and measure the amount of change thereof. When the changing property of the dye label is a chromogenic property, a spectrophotometer or the like can be used to detect the presence of change of the chromogenic property and measure the amount of change thereof.

Preferred examples of a method for calculating the degree of the increase of the methylation level of the substrate compound or the like of the present invention from the degree of the change of the fluorescence property or chromogenic property of the dye label measured in the step (d) can include a method which involves first determining the degree of the decrease of the cleavage activity of the peptidase using the substrate compound or the like of the present invention as a substrate and calculating, from the degree, the degree of the increase of the methylation level of the substrate compound or the like of the present invention. Preferred examples of a method for determining the degree of the decrease of the cleavage activity of the peptidase using the substrate compound or the like of the present invention as a substrate from the degree of the change of the fluorescence property or chromogenic property of the dye label can include a method which involves determining to what extent the amount of the dye label A (the signal intensity of the dye label A) decreases compared to the amount of the dye label A (the signal intensity of the dye label A) for control when the dye label to be measured is the dye label A (a dye label whose fluorescence property or chromogenic property has been changed by the cleavage of the amide bond in the substrate compound or the like by peptidase) and can include a method which involves determining to what extent the amount of the dye label B (the signal intensity of the dye label B) increases compared to the amount of the dye label B (the signal intensity of the dye label B) for control when the dye label to be measured is the dye label B (a dye label in which the amide bond has not been cleaved by peptidase because of the methylation of the ε amino group of a lysine residue in the substrate compound or the like). Here, "the amount of the dye label A or the amount of the dye label B (the signal intensity of the dye label A or B) for control" means the amount of the dye label A or the amount of the dye label B when the substrate compound or the like of the present invention used in the step (b) is similarly exposed to peptidase while not contacting the sample (that is, while not methylating the ε amino group of the lysine residue in the substrate compound or the like of the present invention). The substrate compound or the like of the present invention is decreased in susceptibility to peptidase when the methylation level (the degree of the methylation of the ε amino group of K) is increased; thus, the degree of the increase of the methylation level of the substrate compound or the like of the present invention can be calculated based on the degree of the decrease of the cleavage activity of the peptidase.

The step (e) is not particularly limited provided that it is a step of evaluating the degree of the increase of the methylation level in the step (d) as the degree of histone methyltransferase activity in the sample. The degree of the increase of the methylation level in the step (d) depends on the histone methyltransferase activity in the sample; thus, the degree of the increase of the methylation level can be evaluated as the degree of histone methyltransferase activity in the sample.

5. "Method for Screening for Compounds Inhibiting Histone Methyltransferase Activity" of the Present Invention The method for screening for compounds inhibiting histone methyltransferase activity according to the present invention is not particularly limited provided that it comprises the steps of:

(a) providing the substrate compound or the like of the present invention;

(b) contacting the substrate compound or the like of the present invention with histone methyltransferase in the presence of a test compound under conditions required for methylation reaction by histone methyltransferase;

(c) exposing the substrate compound or the like of the present invention to peptidase after the step (b);

(d) measuring the degree of the change of the fluorescence property or chromogenic property of the dye label after the step (c) to calculate the degree of the increase of the methylation level of the substrate compound or the like of the present invention, based on the degree of the decrease of the cleavage activity of the peptidase that uses the substrate compound or the like of the present invention as a substrate; and (e) selecting a test compound for which the degree of the increase of the methylation level of the substrate compound or the like of the present invention in the step (d) is low compared to the degree of the increase of the methylation level of the substrate compound or the like of the present invention in the absence of the test compound.

By such a method, compounds inhibiting histone methyltransferase activity can be highly simply and sensitively screened. The screening method is of great significance because a histone methyltransferase inhibitor is expected as a therapeutic agent for diseases such as cancer and neurodegenerative disease and to be applied to regenerative medicine using iPS cells.

The step (a) is not particularly limited provided that it is a step of providing the substrate compound or the like of the present invention, and includes a step of preparing the substrate compound or the like of the present invention.

The step (b) is not particularly limited provided that it is a step of contacting the substrate compound or the like of the present invention with histone methyltransferase in the presence of a test compound under conditions required for methylation reaction by histone methyltransferase; however, preferred examples thereof can include contacting the substrate compound or the like of the present invention with histone methyltransferase in the presence of a test compound in a solution meeting conditions required for methylation reaction by histone methyltransferase. The conditions required for methylation reaction by histone methyltransferase are as described in the item 4. The test compound is not particularly limited; however, it can preferably use each compound from compound libraries in Chemical Biology Research Initiative, The University of Tokyo and the like. The steps (c) and (d) are the same as the steps (c) and (d) described in the item 4.

The step (e) is not particularly limited provided that it is a step of selecting a test compound for which the degree of the increase of the methylation level of the substrate compound or the like of the present invention in the step (d) (hereinafter, also indicated as "degree A") is low compared to the degree of the increase of the methylation level of the substrate compound or the like of the present invention in the absence of the test compound (hereinafter, also indicated as "degree B"). Such a test compound can be evaluated as being a compound inhibiting histone methyltransferase activity. The low ratio of the degree A to the degree B is not particularly limited; however, preferred examples thereof can include a ratio of the degree A to the degree B of 80% or less, preferably 70% or less, more preferably 60% or less, more preferably 50% or less, more preferably 40% or less, more preferably 30% or less, more preferably 20% or less, more preferably 10% or less when the concentration of the test compound is 10 μM.

The present invention will be more specifically described below with reference to Examples. However, the present invention is not intended to be limited thereto.

EXAMPLE 1

[Decreased Susceptibility to Peptidase Due to Methylation of Substrate compound of the Present Invention—1]

To determine whether a methylation of the substrate compound of the present invention actually decreases susceptibility to a peptidase, a mixing assay between the substrate compound of the present invention and the peptidase was performed. Specifically, it was carried out by the following method.

Distilled water was added to 10 μL of 2×HMT buffer (100 mM Tris-HCl (pH 8.5), 20 mM $MgCl_2$, 40 mM KCl, 20 mM 2-mercaptoethanol, 500 mM sucrose) and 1 μL of a BocLysMCA solution to adjust the total volume to 20 μL. To the resultant solution was added 30 μL of a peptidase solution (20 mg/mL trypsin or 20 mAU/mL lysyl endopeptidase), which was then mixed and incubated at 37° C. for 15 minutes. Then, the fluorescence intensity of the solution was measured at an excitation wavelength ($\lambda$ex) of 390 nm and a fluorescence wavelength ($\lambda$em) of 460 nm. The wavelength is a wavelength for detecting AMC (7-amino-4-methylcoumarin) released by the cleavage of the amide bond between Lys and MCA of BocLysMCA. The fluorescence intensity of AMC was similarly measured by performing a mixing assay by the same method as the above method except for using monomethylated BocLysMCA (i.e., "BocLys(Me)MCA"), dimethylated BocLysMCA (i.e., "BocLys(Me)$_2$MCA"), or trimethylated BocLysMCA (i.e., "BocLys(Me)$_3$MCA") in place of BocLysMCA.

Figure 7:
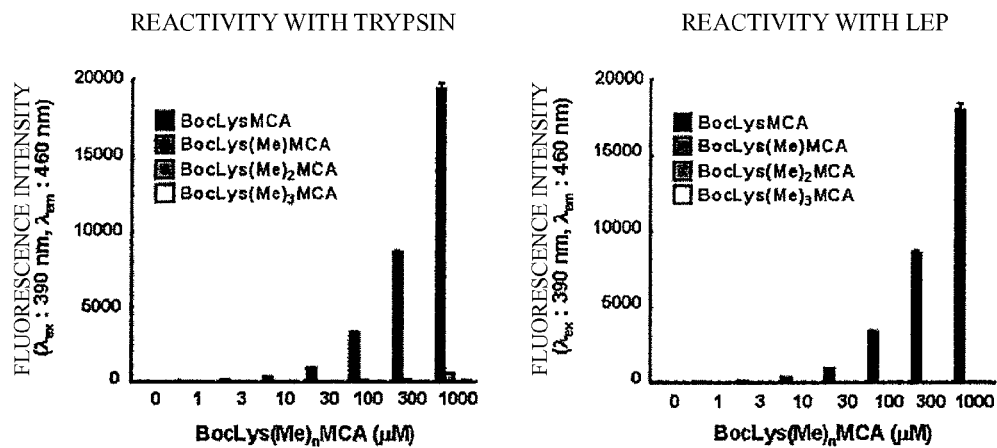
FIG. 7 is a pair of graphs showing the results of a test confirming decreased susceptibility to peptidase due to the methylation of the substrate compound of the present invention. The left panel of FIG. 7 indicates the results showing susceptibility to trypsin (reactivity with trypsin), and the right panel indicates the results showing susceptibility to lysyl endopeptidase (reactivity with lysyl endopeptidase).

The results of measuring the fluorescence intensity in these mixing assays are shown in FIG. 7. The left panel of FIG. 7 indicates the results showing susceptibility to trypsin (reactivity with trypsin), and the right panel indicates the results showing susceptibility to lysyl endopeptidase (reactivity with lysyl endopeptidase). The results of FIG. 7 showed that the addition of each of trypsin and lysyl endopeptidase to BocLysMCA increased the fluorescence intensity of AMC in a manner dependent on the concentration of peptidase. In contrast, the fluorescence intensity of AMC was significantly weak when each of the peptidases was added for the use of any of 3 types of methylated BocLysMCAs compared to for the use of BocLysMCA. For example, when 1,000 μM BocLys(Me)$_n$MCA (wherein n=0, 1, 2, or 3) and trypsin were used, the fluorescence intensities of BocLys(Me)MCA, BocLys(Me)$_2$MCA, and BocLys(Me)$_3$MCA when the fluorescence intensity for the use of BocLysMCA was set to 100% were only 2.7%, 0.12%, and 0.24%, respectively; when 1,000 μM BocLys(Me)$_n$MCA (wherein n=0, 1, 2, or 3) and lysyl endopeptidase were used, the fluorescence intensities of BocLys(Me)MCA, BocLys(Me)$_2$MCA, and BocLys(Me)$_3$MCA when the fluorescence intensity for the use of BocLysMCA was set to 100% were only 0.096%, 0.053%, and 0.25%, respectively.

The above results showed that BocLysMCA falling within the substrate compound of the present invention was decreased in susceptibility to peptidase when (the ε amino group of) the lysine residue thereof was methylated.

EXAMPLE 2

[Influence of Trypsin Inhibitor on Reaction Between Substrate compound of the Present Invention and Peptidase]

Then, to determine whether the fluorescence intensity of AMC obtained in the mixing assay of Example 1 depended on peptidase activity, a mixing assay was performed. Specifically, it was carried out by the following method.

Distilled water was added to 10 μL of 2×HMT buffer (100 mM Tris-HCl (pH 8.5), 20 mM MgCl$_2$, 40 mM KCl, 20 mM 2-mercaptoethanol, 500 mM sucrose), 1 μL of a BocLysMCA solution, and 5 μL of a trypsin inhibitor solution to adjust the total volume to 20 μL. To the resultant solution was added 30 μL of a peptidase solution (20 mg/mL trypsin or 20 mAU/mL lysyl endopeptidase), which was then mixed and incubated at 37° C. for 15 minutes. Then, the fluorescence intensity of the solution was measured at an excitation wavelength (λex) of 390 nm and a fluorescence wavelength (λem) of 460 nm.

Figure 8:
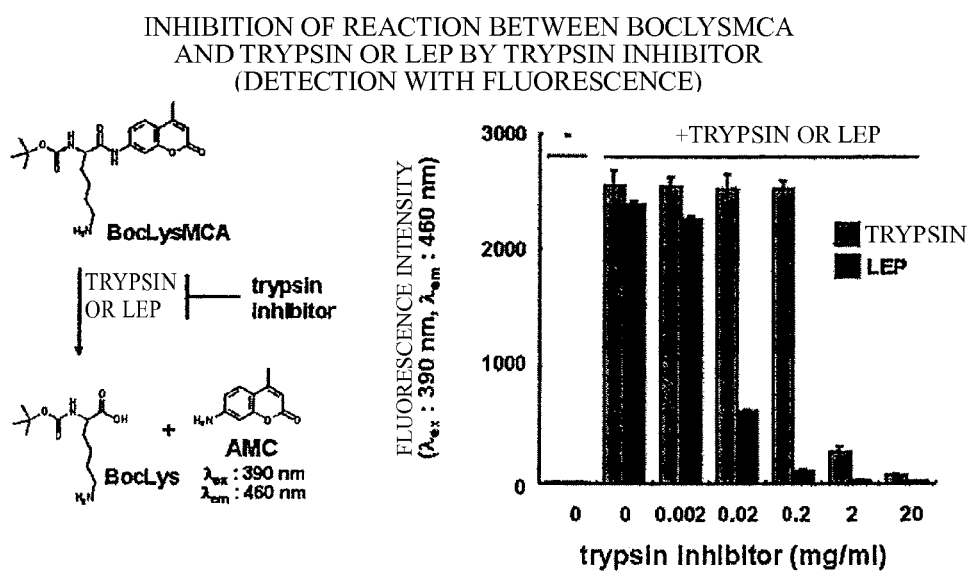
FIG. 8 is a drawing showing the results of a test confirming the influence of a trypsin inhibitor on the reaction between the substrate compound of the present invention and a peptidase.

The results of measuring the fluorescence intensity in these mixing assays are shown in FIG. 8. As shown in FIG. 8, the addition of the trypsin inhibitor significantly decreased the fluorescence intensity of AMC for each of trypsin and lysyl endopeptidase when the concentration of the trypsin inhibitor reached a certain level or more.

The above results determined that the fluorescence intensity of AMC obtained in the mixing assay of Example 1 depended on peptidase activity.

EXAMPLE 3

[Determination of Reactivity Between Substrate Compound of the Present Invention and Peptidase]

To analyze the details of the reaction between the substrate compound of the present invention and a peptidase in the mixing assay of Example 1, analysis by LC/MS was carried out. Specifically, it was carried out by the following method.

Distilled water was added to 10 μL of 2×HMT buffer (100 mM Tris-HCl (pH 8.5), 20 mM MgCl$_2$, 40 mM KCl, 20 mM 2-mercaptoethanol, 500 mM sucrose) and 1 μL of a BocLysMCA solution to adjust the total volume to 20 μL. To the resultant solution was added 30 μL of a peptidase solution (20 mg/mL trypsin or 20 mAU/mL lysyl endopeptidase), which was then mixed and incubated at 37° C. for 15 minutes. Then, the solution was applied to a liquid chromatograph mass spectrometer (LC/MS) for analysis. Analysis was performed by the same method as that for the above analysis except for using monomethylated BocLysMCA (i.e., "BocLys(Me)MCA"), dimethylated BocLysMCA (i.e., "BocLys(Me)$_2$MCA"), or trimethylated BocLysMCA (i.e., "BocLys(Me)$_3$MCA") in place of BocLysMCA. Analysis was also carried out by the same method except for using, in place of the above-described peptidase solution, an equal volume of distilled water.

As a result of this analysis, a peak for BocLysMCA was detected when peptidase was not used for BocLysMCA, while the peak for BocLysMCA disappeared and a peak for BocLys and a peak for AMC were detected instead when trypsin was used or when lysyl endopeptidase was used. This determined that most BocLysMCA was hydrolyzed to BocLys and AMC by trypsin or lysyl endopeptidase. In contrast, when BocLys(Me)MCA, BocLys(Me)$_2$MCA, and BocLys(Me)$_3$MCA resulting from the methylation of the ε amino group of the lysine residue in BocLysMCA were treated with trypsin or lysyl endopeptidase, peaks for their degradation products were little detected, showing almost no occurrence of hydrolysis.

EXAMPLE 4

[Measurement of Histone Methyltransferase Activity Using Substrate Compound of the Present Invention]

To examine whether the substrate compound of the present invention can actually be used for the measurement of histone methyltransferase activity in vitro, an assay was attempted for measuring the histone methyltransferase activity. Specifically, it was carried out by the following method.

Distilled water was added to 10 μL of 2×HMT buffer (100 mM Tris-HCl (pH 8.5), 20 mM MgCl$_2$, 40 mM KCl, 20 mM 2-mercaptoethanol, 500 mM sucrose), 2 μL of a BSA solution (30 μg/mL), and a predetermined concentration (final concentration: 0, 0.015, 0.05, or 0.15 μg/μL) of a histone methyltransferase (G9a) solution to adjust the total volume to 16 μL. Thereafter, the resultant solution was incubated at room temperature for 1 hour. Then, 2 μL of S-adenosylmethionine (SAM) (10 mM) and 2 μL of BocLysMCA (final concentration: 0.009 mM, 0.03 mM, or 0.09 mM) were added thereto, which was mixed and then incubated at 37° C. for 1 hour. Subsequently, 30 μL of a trypsin solution (20 mg/mL) was added thereto, followed by incubation at 37° C. for 15 minutes. The fluorescence intensity of the solution was measured at an excitation wavelength (λex) of 390 nm and a fluorescence wavelength (λem) of 460 nm.

Figure 9:
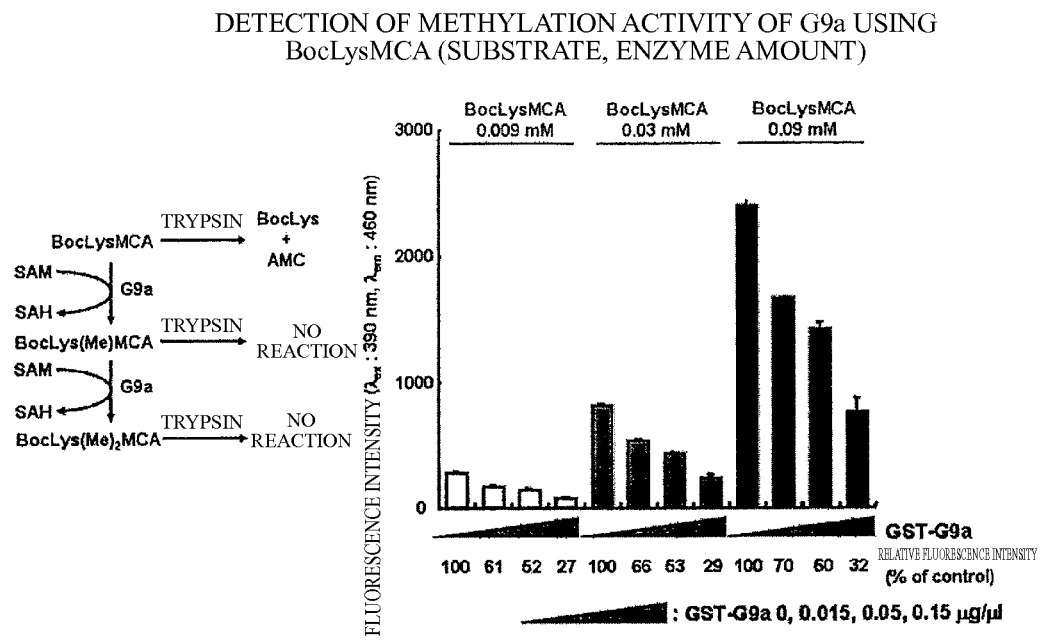
FIG. 9 is a graph showing the results of measuring histone methyltransferase activity using the substrate compound of the present invention. The concentrations of the substrate compound of the present invention and the histone methyltransferase are varied.

The results of measuring the fluorescence intensity in the assay for measuring histone methyltransferase activity are shown in FIG. 9. As shown in FIG. 9, when the concentration of BocLysMCA was in the range of 0.009 mM to 0.09 mM, the fluorescence intensity of AMC decreased in a manner dependent on the concentration of the histone methyltransferase G9a. That is, it was shown that the methylation activity of the histone methyltransferase G9a could be measured using the degree of the decrease of the fluorescence intensity of AMC (the degree of the decrease of the cleavage activity of trypsin as a peptidase) as an indicator.

Figure 10:
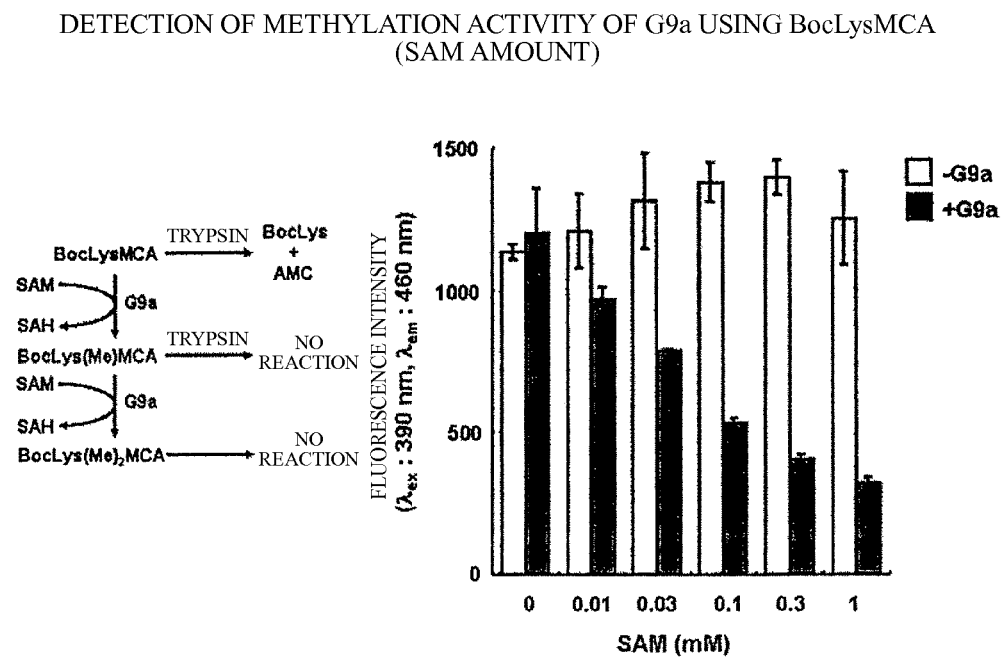
FIG. 10 is a graph showing the results of measuring histone methyltransferase activity using the substrate compound of the present invention. The concentration of SAM as a methyl group donor is varied.

Then, FIG. 10 shows the results of measuring fluorescence intensity when SAM as a methyl group donor was used in any of various concentrations in the above assay for measuring histone methyltransferase activity. As shown in the result in FIG. 10, the addition of the histone methyltransferase G9a (+G9a) decreased the fluorescence intensity of AMC in a manner dependent on the concentration of SAM, while no change in the fluorescence intensity of AMC depending on the SAM concentration was observed when G9a was not added (–G9a).

The above results showed that the substrate compound of the present invention could actually be used for measuring histone methyltransferase activity in vitro and that the measurement was highly simple and sensitive.

EXAMPLE 5

[Determination of Reaction in Assay for Measuring Histone Methyltransferase Activity]

To analyze the details of reaction in the assay for measuring histone methyltransferase activity of Example 4, analysis by LC/MS was carried out. Specifically, it was carried out by the following method.

Distilled water was added to 10 µL of 2×HMT buffer (100 mM Tris-HCl (pH 8.5), 20 mM $MgCl_2$, 40 mM KCl, 20 mM 2-mercaptoethanol, 500 mM sucrose), 2 µL of a BSA solution (30 µg/mL), and a predetermined concentration (final concentration: 0.15 µg/µL) of a histone methyltransferase (G9a) solution to adjust the total volume to 16 µL. Thereafter, the resultant solution was incubated at room temperature for 1 hour. Then, 2 µL of S-adenosylmethionine (SAM) (10 mM) and 2 µL of BocLysMCA (final concentration: 0.09 mM) were added thereto, which was mixed and then incubated at 37° C. for 1 hour. Subsequently, 30 µL of a trypsin solution (20 mg/mL) or a lysyl endopeptidase solution (20 mAU/mL) was added thereto, followed by incubation at 37° C. for 15 minutes. Then, the solution was applied to a liquid chromatograph mass spectrometer (LC/MS) for analysis (+SAM/+G9a). Analysis using distilled water in place of the SAM solution in the above analysis (–SAM/+G9a), analysis using distilled water in place of the G9a solution (+SAM/–G9a), and analysis using distilled water in place of the SAM solution and the G9a solution (–SAM/–G9a) were also carried out. In addition, analysis when no trypsin or lysyl endopeptidase is used was also carried out.

Figure 11:
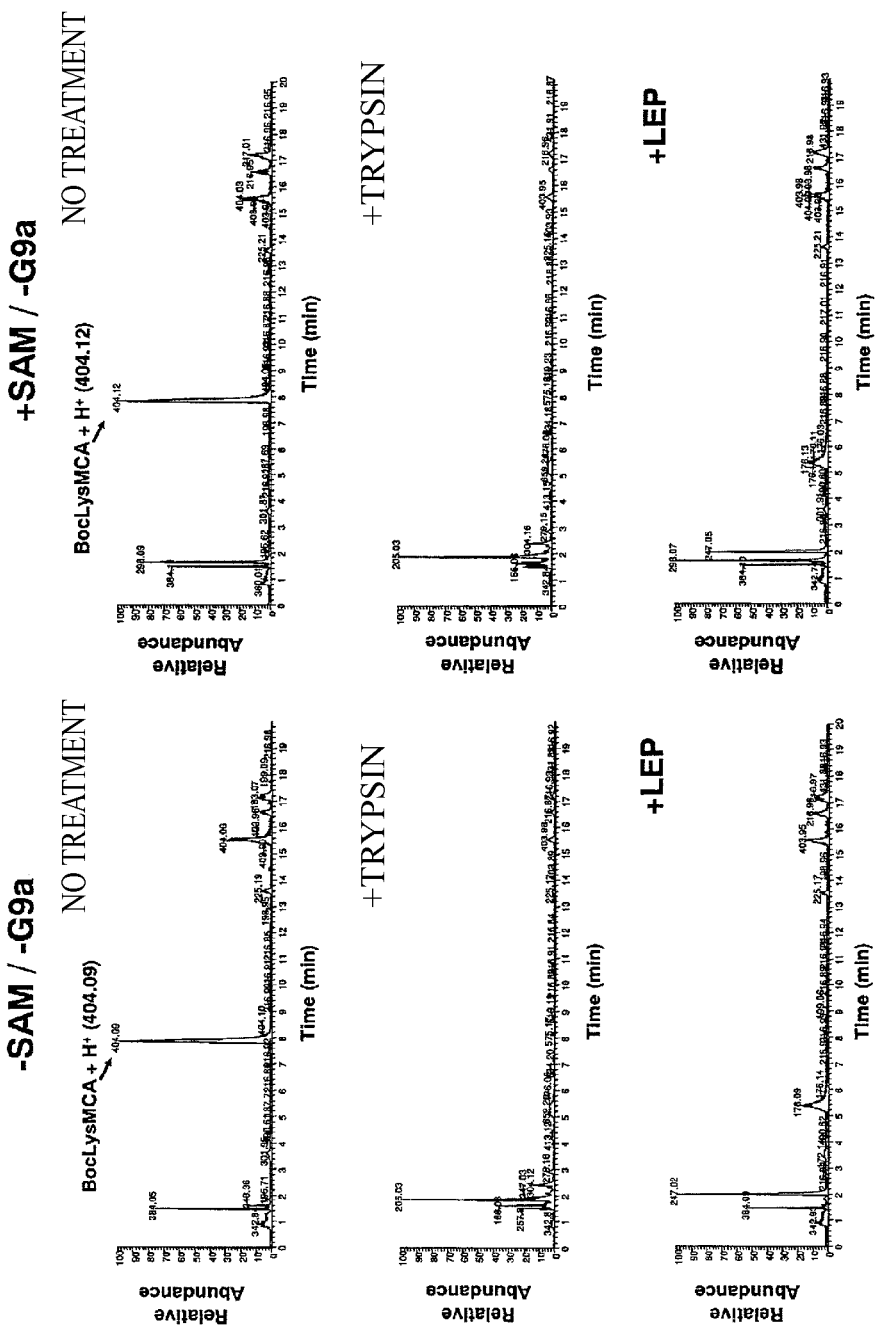
FIG. 11 is a series of graphs showing the results of the analysis of reaction in an assay for measuring histone methyltransferase activity (in the absence of G9a as a histone methyltransferase) by LC/MS. The top panel shows the analysis results for no use of peptidase (no treatment); the middle panel shows the analysis results for the use of trypsin (+trypsin) as the peptidase; and the bottom panel shows the analysis results for the use of lysyl endopeptidase (+LEP) as the peptidase.
Figure 12:
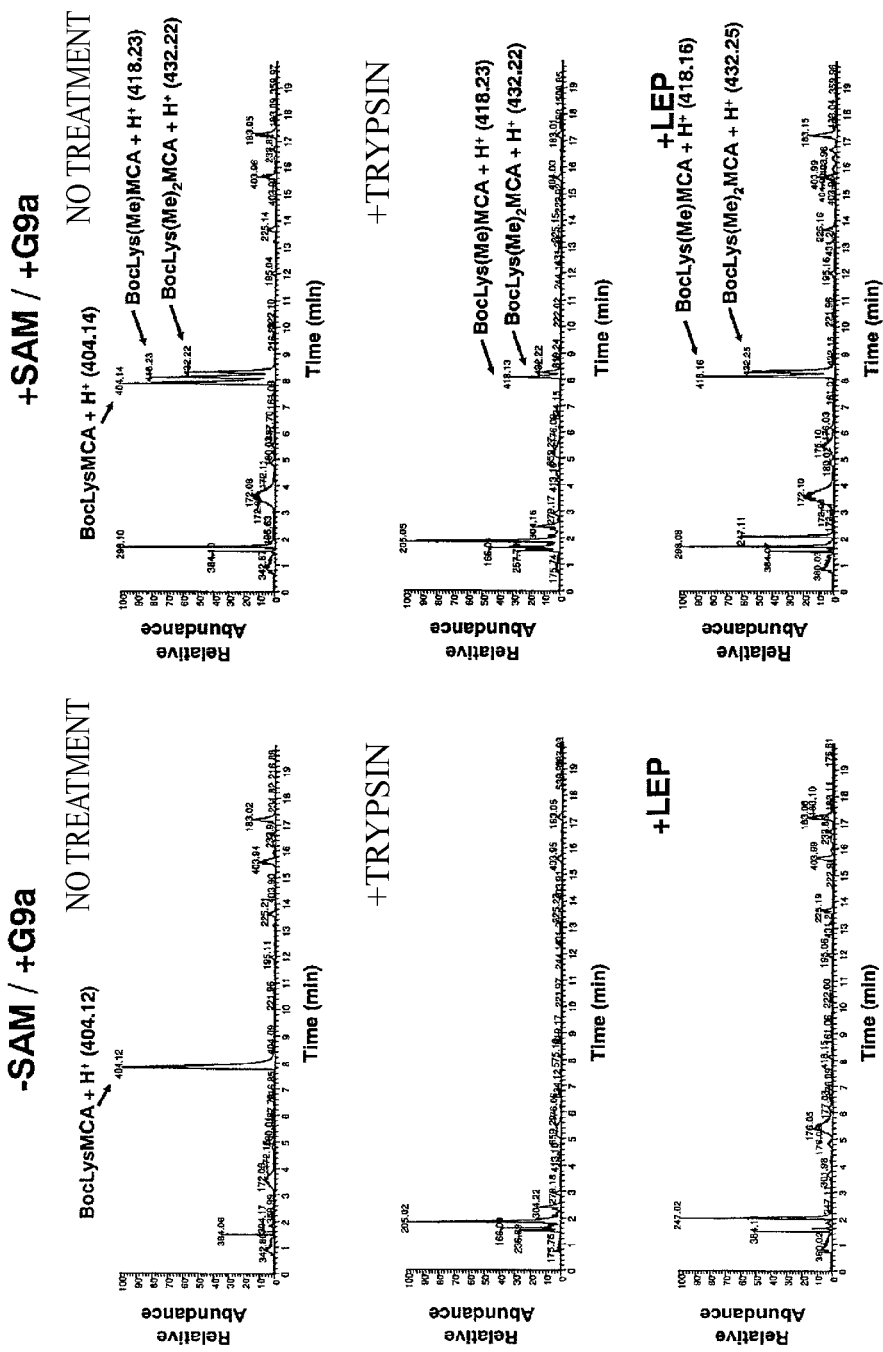
FIG. 12 is a series of graphs showing the results of the analysis of reaction in an assay for measuring histone methyltransferase activity (in the presence of G9a as a histone methyltransferase) by LC/MS. The top panel shows the analysis results for no use of peptidase (no treatment); the middle panel shows the analysis results for the use of trypsin (+trypsin) as the peptidase; and the bottom panel shows the analysis results for the use of lysyl endopeptidase (+LEP) as the peptidase.

The results of analysis in the case of –SAM/–G9a is shown in the left panel of FIG. 11; the results of analysis in the case of +SAM/–G9a is shown in the right panel of FIG. 11; the results of analysis in the case of –SAM/+G9a is shown in the left panel of FIG. 12; and the results of analysis in the case of +SAM/+G9a is shown in the right panel of FIG. 12. In each of FIGS. 11 and 12, the top panel represents the results of analysis when peptidase was not used; the middle panel represents the results of analysis when trypsin was used as a peptidase; and the bottom panel represents the results of analysis when lysyl endopeptidase was used as a peptidase. The results of FIGS. 11 and 12 showed that in the case of the absence of any of SAM and G9a (–SAM/–G9a, +SAM/–G9a, or –SAM/+G9a), a peak for BocLysMCA was detected when a peptidase was not added and peaks for BocLys and AMC were detected when a peptidase (trypsin or lysyl endopeptidase) was added. In contrast, in the case of the addition of both SAM and G9a (+SAM/+G9a), peaks for BocLys(Me)MCA and BocLys(Me)$_2$MCA as well as BocLysMCA were detected when a peptidase was not added and only a peak for unmethylated BocLysMCA disappeared and a peak for BocLys(Me)MCA and BocLys(Me)$_2$MCA remained when a peptidase was added.

The above results showed that the reactions supposed by the present inventor occurred in the assay for measuring histone methyltransferase activity. That is, it was shown that the methylation of BocLysMCA produced no cleavage thereof by peptidase, while BocLysMCA was cleaved by peptidase to form BocLys and AMC.

EXAMPLE 6

[Examination of Substrate Specificity of Histone Methyltransferase Using Peptidyl MCA—1]

To determine whether the substrate specificity of a histone methyltransferase could be examined by an assay for measuring histone methyltransferase activity using a peptidyl substrate compound (peptidyl MCA) in which X in the substrate compound of the present invention represented one or more amino acid residues (peptide), the assay for measuring histone methyltransferase activity was carried out. Specifically, it was carried out by the following method.

Peptidyl MCAs as shown in FIG. 13 were first prepared. Ac-histone H3 (1-4)-MCA is a substrate compound, wherein in the general formula (I), the protecting group ($R_1$) is an acetyl group; X—K is a peptide consisting of amino acid residues of amino acid 1 to 4 of human histone H3 (ARTK; SEQ ID NO: 1); and the dye label ($R_2$) is MCA. Ac-histone H3 (5-9)-MCA is a substrate compound, wherein in the general formula (I), the protecting group ($R_1$) is an acetyl group; X—K is a peptide consisting of amino acid residues of amino acid 5 to 9 of human histone H3 (QTARK; SEQ ID NO: 2); and the dye label ($R_2$) is MCA. Ac-histone H3 (1-9)-MCA is a substrate compound, wherein in the general formula (I), the protecting group ($R_1$) is an acetyl group; X—K is a peptide consisting of amino acid residues of amino acid 1 to 9 of human histone H3 (ARTKQTARK; SEQ ID NO: 3); and the dye label ($R_2$) is MCA. Ac-histone H3 (7-9/25-27)-MCA is a substrate compound, wherein in the general formula (I), the protecting group ($R_1$) is an acetyl group; X—K is a peptide consisting of amino acid residues of amino acid 7 to 9 or 25 to 27 of human histone H3 (ARK); and the dye label ($R_2$) is MCA. Ac-histone H3 (23-27)-MCA is a substrate compound, wherein in the general formula (I), the protecting group ($R_1$) is an acetyl group; X—K is a peptide consisting of amino acid residues of amino acid 23 to 27 of human histone H3 (KAARK; SEQ ID NO: 4); and the dye label ($R_2$) is MCA. Ac-histone H3 (19-27)-MCA is a substrate compound, wherein in the general formula (I), the protecting group ($R_1$) is an acetyl group; X—K is a peptide consisting of amino acid residues of amino acid 19 to 27 of human histone H3 (QLATKAARK; SEQ ID NO: 5); and the dye label ($R_2$) is MCA. Ac-p53 (367-372)-MCA is a substrate compound, wherein in the general formula (I), the protecting group ($R_1$) is an acetyl group; X—K is a peptide consisting of amino acid residues of amino acid 369 to 372 of human p53 (LKSK; SEQ ID NO: 6), and the dye label ($R_2$) is MCA. Note that G9a uses the lysine residue of amino acid 9 (histone H3K9) or the lysine residue of amino acid 27 (histone H3K27) of histone H3 as a methylation site, and Set9 uses the lysine residue of amino acid 4 of histone 3 (histone H3K4) or the lysine residue of amino acid 372 of p53 protein (p53K372) as a methylation site.

When G9a was adopted as a histone methyltransferase, the following method was used. 10 µL of 2×HMT buffer (100 mM Tris-HCl (pH 8.5), 20 mM $MgCl_2$, 40 mM KCl, 20 mM 2-mercaptoethanol, 500 mM sucrose), 0.4 µL of a BSA solution (150 µg/mL), 4.5 µL of GST-mG9a (0, 0.022 to 0.66 µg/µL), and 1.1 µL of distilled water were mixed and then incubated at room temperature for 1 hour. Then, 2 µL of SAM (10 mM) and 2 µL of a peptidyl MCA solution (0.6 mM) were added thereto, which was then incubated at 37° C. for 1 hour. Thereafter, 30 µL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of GST-mG9a during the measurement of fluorescence intensity was 0, 0.005, 0.015, 0.05, or 0.15 µg/µL. The results of the assay for measuring histone methyltransferase activity are shown in the left panel of FIG. 14. The results in the left panel of FIG. 14 showed that little methylation occurred when Ac-histone H3 (1-4)-MCA or Ac-p53 (369-372)-MCA was used, while methylation often occurred when Ac-histone H3 (5-9)-MCA, Ac-histone H3(1-9)-MCA, Ac-histone H3 (7-9/25-27)-MCA, Ac-histone H3 (23-27)-MCA, or Ac-histone H3(19-27)-MCA was used.

When Set9 was adopted as a histone methyltransferase, the following method was used. 10 µL of 2×HMT buffer (100 mM Tris-HCl (pH 8.5), 20 mM $MgCl_2$, 40 mM KCl, 20 mM 2-mercaptoethanol, 500 mM sucrose), 2 µL of a BSA solution (30 µg/mL), 3 µL of His-Set9 (0, 0.33 to 10 µg/µL), and 1 µL of distilled water were mixed and then incubated at room temperature for 1 hour. Then, 2 µL of SAM (10 mM) and 2 µL of a peptidyl MCA solution (0.6 mM) were added thereto, which was then incubated at 37° C. for 1 hour. Thereafter, 30 µL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of His-Set9 during the measurement of fluorescence intensity was 0, 0.05, 0.15, 0.5, or 1.5 µg/µL. The results of the assay for measuring histone methyltransferase activity are shown in the right panel of FIG. 14. The results in the right panel of FIG. 14 showed that little methylation occurred when Ac-histone H3 (5-9)-MCA, Ac-histone H3 (1-9)-MCA, Ac-histone H3 (7-9/25-27)-MCA, Ac-histone H3 (23-27)-MCA, or Ac-histone H3 (19-27)-MCA was used, while methylation often occurred when Ac-histone H3 (1-4)-MCA or Ac-p53 (369-372)-MCA was used.

The results in the left panel and the right panel of FIG. 14 showed that whereas, when K amide-bound to MCA in a peptidyl MCA was a methylation site for histone methyltransferase, methylation often occurred in the K, when the K was not a methylation site for histone methyltransferase, little methylation occurred in the K. That is, it was shown that an assay for measuring histone methyltransferase activity could be performed using a peptidyl MCA resulting from adding a peptide N-terminally to the lysine residue (K) to evaluate the substrate specificity of the histone methyltransferase.

EXAMPLE 7

[Examination of Substrate Specificity of Histone Methyltransferase Using Peptidyl MCA—2]

The lysine residue of amino acid 302 (K302) of estrogen receptor a (ERα) as a nuclear receptor has previously been reported to be methylated by Set9 (Molecular Cell, 30: 336-347, 2008). Accordingly, an assay for measuring histone methyltransferase activity was carried out in order to evaluate the substrate specificity of Set9 using a sequence in the vicinity of K302 of ERα and a sequence derived from another nuclear receptor (androgen receptor or glucocorticoid receptor) having homology to the sequence. Specifically, it was carried out by the following method.

Peptidyl MCAs as shown in FIG. 15 were first prepared. Ac-ERα (299-302)-MCA is a substrate compound, wherein in the general formula (I), the protecting group ($R_1$) is an acetyl group; X—K is a peptide consisting of amino acid residues of amino acid 299 to 302 of human ERα (KRSK; SEQ ID NO: 8); and the dye label ($R_2$) is MCA. Ac-ERα (297-302)-MCA is a substrate compound, wherein in the general formula (I), the protecting group ($R_1$) is an acetyl group; X—K is a peptide consisting of amino acid residues of amino acid 297 to 302 of human ERα (MIKRSK; SEQ ID NO: 9); and the dye label ($R_2$) is MCA. Ac-AR (630-633)-MCA is a substrate compound, wherein in the general formula (I), the protecting group ($R_1$) is an acetyl group; X—K is a peptide consisting of amino acid residues of amino acid 630 to 633 of human androgen receptor (AR) (RKLK; SEQ ID NO: 10); and the dye label ($R_2$) is MCA. Ac-AR (628-633)-MCA is a substrate compound, wherein in the general formula (I), the protecting group ($R_1$) is an acetyl group; X—K is a peptide consisting of amino acid residues of amino acid 628 to 633 of human AR (GARKLK; SEQ ID NO: 11); and the dye label ($R_2$) is MCA. Ac-GR (491-494)-MCA is a substrate compound, wherein in the general formula (I), the protecting group ($R_1$) is an acetyl group; X—K is a peptide consisting of amino acid residues of amino acid 491 to 494 of human glucocorticoid receptor (GR) (RKTK; SEQ ID NO: 12); and the dye label ($R_2$) is MCA. Ac-GR (489-494)-MCA is a substrate compound, wherein in the general formula (I), the protecting group ($R_1$) is an acetyl group; X—K is a peptide consisting of amino acid residues of amino acid 489 to 494 of human GR (EARKTK; SEQ ID NO: 13); and the dye label ($R_2$) is MCA. Ac-p53 (369-372)-MCA is as described above. Ac-p53 (367-372)-MCA is a substrate compound, wherein in the general formula (I), the protecting group ($R_1$) is an acetyl group; X—K is a peptide consisting of amino acid residues of amino acid 367 to 372 of human p53 (SHLKSK; SEQ ID NO: 7); and the dye label ($R_2$) is MCA. Ac-histone H3 (1-9)-MCA is as described above.

When G9a was adopted as a histone methyltransferase, the following method was used. 10 µL of 2×HMT buffer (100 mM Tris-HCl (pH 8.5), 20 mM $MgCl_2$, 40 mM KCl, 20 mM 2-mercaptoethanol, 500 mM sucrose), 0.4 µL of a BSA solution (150 µg/mL), 3.6 µL of GST-mG9a (0, 0.028, 0.083, 0.28, 0.83 µg/µL), and 4 µL of distilled water were mixed and then incubated at room temperature for 1 hour. Then, 1 µL of SAM (20 mM) and 1 µL of a peptidyl MCA solution (1.2 mM) were added thereto, which was then incubated at 37° C. for 1 hour. Thereafter, 30 µL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of GST-mG9a during the measurement of fluorescence intensity was 0, 0.005, 0.015, 0.05, or 0.15 µg/µL. The results of the assay for measuring histone methyltransferase activity are shown in the left panel of FIG. 16.

When Set9 was adopted as a histone methyltransferase, the following method was used. 10 µL of 2×HMT buffer (100 mM Tris-HCl (pH 8.5), 20 mM $MgCl_2$, 40 mM KCl, 20 mM 2-mercaptoethanol, 500 mM sucrose), 0.4 µL of a BSA solution (150 µg/mL), 5.9 µL of His-Set9 (0, 0.051, 0.17, 0.51, 1.7 µg/µL), and 1.7 µL of distilled water were mixed and then incubated at room temperature for 1 hour. Then, 1 µL of SAM (20 mM) and 1 µL of a peptidyl MCA solution (1.2 mM) were added thereto, which was then incubated at 37° C. for 1 hour. Thereafter, 30 µL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of His-Set9 during the measurement of fluorescence intensity was 0, 0.015, 0.05, 0.15, or 0.5 μg/μL. The results of the assay for measuring histone methyltransferase activity are shown in the right panel of FIG. 16.

As shown in the right panel of FIG. 16, the order of high reactivity with Set 9 was Ac-ERα (299-302)-MCA, Ac-ERα (297-302)-MCA, Ac-p53 (369-372)-MCA, Ac-GR (491-494)-MCA, Ac-p53 (367-372)-MCA or Ac-AR (628-633)-MCA, and Ac-AR (630-633)-MCA or Ac-GR (489-494)-MCA. The results in the left panel of FIG. 16 showed that unlike Ac-histone H3 (1-9)-MCA, the peptidyl MCAs derived from p53 and the nuclear receptors did not react with G9a. These results suggested that the peptidyl MCAs derived from ERα were highly specific for Set9 and very suitable for the evaluation of Set9 activity. The peptidyl MCAs containing K302 of ERα known to be methylated by Set9 exhibited particularly high reactivity with Set9 (right panel of FIG. 16); thus, the assay for measuring histone methyltransferase activity according to the present invention was also shown to be highly sensitive.

EXAMPLE 8

[Activity Evaluation of Histone Methyltransferase Inhibitor Using Peptidyl MCA—1]

To examine whether the activity of a histone methyltransferase inhibitor could be evaluated by an assay for measuring histone methyltransferase activity using a peptidyl MCA, the assay for measuring histone methyltransferase activity was attempted. However, the activity of gliotoxin as a histone methyltransferase inhibitor was evaluated by Western blot, prior to the assay for measuring histone methyltransferase activity. Gliotoxin is known not to inhibit the methylation activity of Set9 but to inhibit the methylation activity of G9a. The results of Western blot are shown in FIG. 17. In conformance with its known properties, gliotoxin did not inhibit the methylation of Set9, but inhibited the methylation of G9a (FIG. 17). The following assay for measuring histone methyltransferase activity was carried out in order to examine whether the same results as those from the Western blot could also be obtained from the assay for measuring histone methyltransferase activity.

When G9a was adopted as a histone methyltransferase, the following method was used. 10 μL of 2×HMT buffer (100 mM Tris-HCl (pH 8.5), 20 mM $MgCl_2$, 40 mM KCl, 20 mM 2-mercaptoethanol, 500 mM sucrose), 0.4 μL of a BSA solution (150 μg/mL), 2 μL of GST-mG9a (0, 0.5 μg/μL), 1 μL of gliotoxin (any of various concentrations) and 2.6 μL of distilled water were mixed and then incubated at room temperature for 1 hour. Then, 2 μL of SAM (10 mM) and 2 μL of a peptidyl MCA (Ac-histone H3 (1-9)-MCA) solution (0.6 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of GST-mG9a during the measurement of fluorescence intensity was 0.05 μg/μL. The results of the assay for measuring histone methyltransferase activity are shown in the middle panel of FIG. 18. The results in the middle panel of Figure showed that the use of G9a whose methylation was inhibited by gliotoxin increased the fluorescence intensity of AMC (that is, the degree of the inhibition of peptidyl MCA methylation) as the concentration of gliotoxin was increased.

When Set9 was adopted as a histone methyltransferase, the following method was used. 10 μL of 2×HMT buffer (100 mM Tris-HCl (pH 8.5), 20 mM $MgCl_2$, 40 mM KCl, 20 mM 2-mercaptoethanol, 500 mM sucrose), 0.4 μL of a BSA solution (150 μg/mL), 4.5 μL of His-Set9 (0, 2.25 μg/μL), 1 μL of gliotoxin (any of various concentrations) and 0.1 μL of distilled water were mixed and then incubated at room temperature for 1 hour. Then, 2 μL of SAM (10 mM) and 2 μL of a peptidyl MCA (Ac-p53 (369-372)-MCA) solution (0.6 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 390 nm and a fluorescence wavelength (λem) of 460 nm. The final concentration of His-Set9 during the measurement of fluorescence intensity was 0.5 μg/μL. The results of the assay for measuring histone methyltransferase activity are shown in the left panel of FIG. 18. The results in the left panel of FIG. 18 showed that the use of Set9 whose methylation was not inhibited by gliotoxin remained to produce the methylation of peptidyl MCAs and the variation of the gliotoxin concentration did not change the fluorescence intensity of AMC (that is, the degree of the inhibition of peptidyl MCA methylation).

Figure 18:
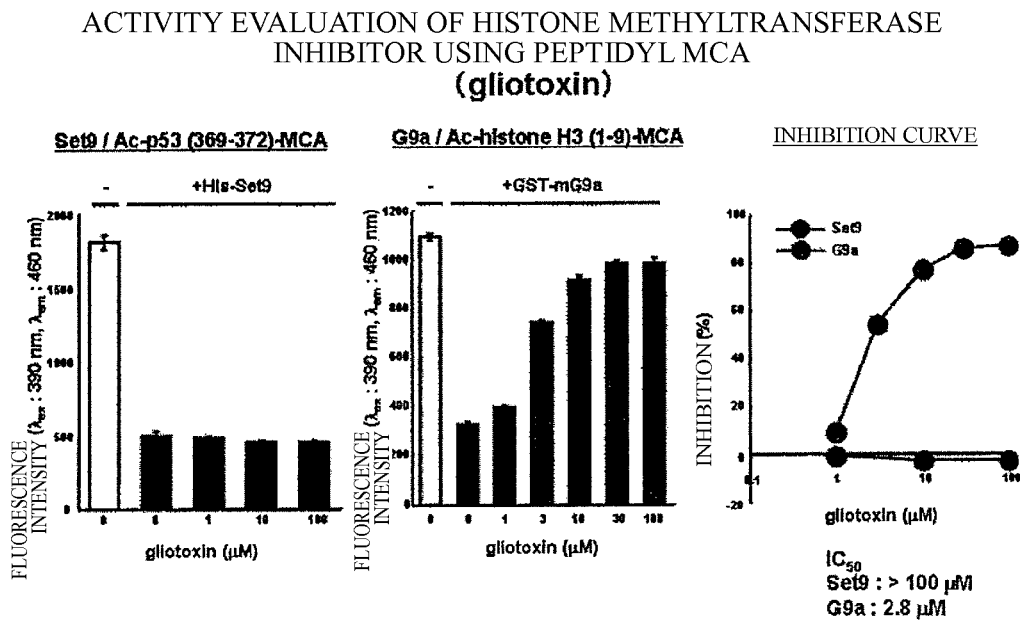
FIG. 18 is a series of graphs showing the results of activity evaluation of a histone methyltransferase inhibitor (gliotoxin) using a peptidyl MCA. The left panel of FIG. 18 shows the results of an assay for measuring histone methyltransferase activity for the use of a histone methyltransferase Set9 and Ac-p53 (369-372)-MCA. The middle panel of FIG. 18 shows the results of an assay for measuring histone methyltransferase activity for the use of a histone methyltransferase G9a and Ac-histone H3 (1-9)-MCA. The right panel of FIG. 18 shows the rates (%) of methylation inhibition by gliotoxin, calculated from the results of the left panel and the middle panel of FIG. 18.

The rate of the inhibition of methylation by gliotoxin was calculated from the results in the left panel and the middle panel of FIG. 18. Specifically, the value (%) was calculated which was obtained by dividing "a value obtained by subtracting "the fluorescence intensity of AMC when peptidase was added but gliotoxin was not added" from "the fluorescence intensity of AMC when both peptidase and gliotoxin were added"" by "a value obtained by subtracting "the fluorescence intensity of AMC when peptidase was added but gliotoxin was not added" from "the fluorescence intensity of AMC when no peptidase or gliotoxin was added"" and multiplying the resultant value by 100. The rate (%) of the inhibition of methylation by gliotoxin is shown in the right panel of FIG. 18. The results showed that the $IC_{50}$ of gliotoxin for G9a was 2.8 μM and the $IC_{50}$ thereof for Set9 was at least higher than 100 μM. These results of FIG. 18 are similar to the results of Western blot in FIG. 17 and show that whereas gliotoxin does not inhibit the methylation activity of Set9, it specifically inhibits the methylation activity of G9a.

EXAMPLE 9

[Activity Evaluation of Histone Methyltransferase Inhibitor Using Peptidyl MCA—2]

To examine whether the activity of a histone methyltransferase inhibitor could be evaluated by an assay for measuring histone methyltransferase activity using a peptidyl MCA even when the histone methyltransferase inhibitor had a low molecular weight, the following assay for measuring histone methyltransferase activity was attempted.

Figure 19:
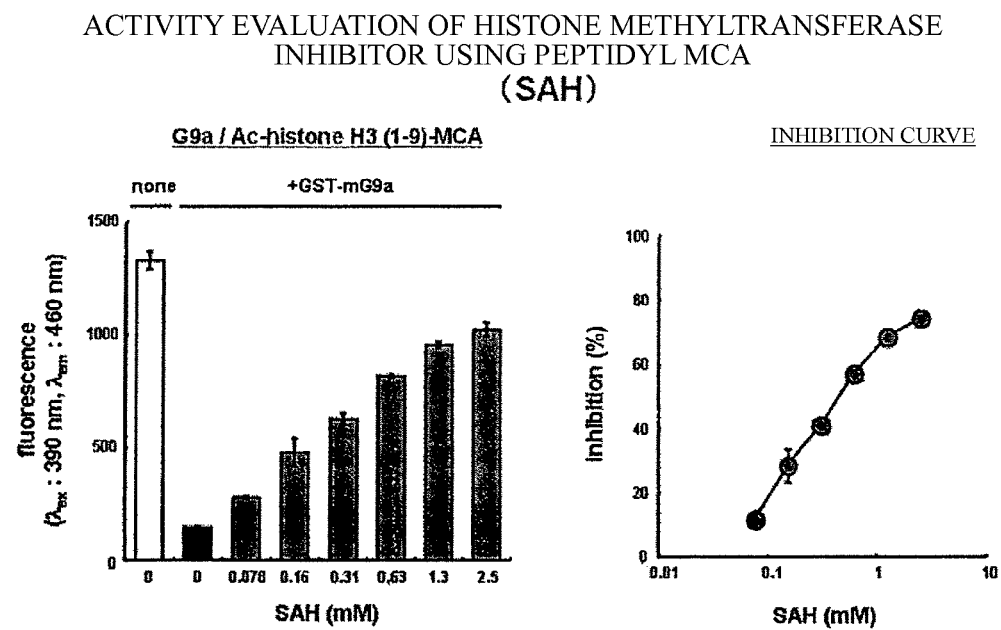
FIG. 19 is a pair of graphs showing the results of activity evaluation of a histone methyltransferase inhibitor (S-adenosyl-L-homocysteine: SAH) using a peptidyl MCA. The left panel of FIG. 19 shows the results of an assay for measuring histone methyltransferase activity for the use of a histone methyltransferase G9a and Ac-histone H3 (1-9)-MCA. The right panel of FIG. 19 shows the rate (%) of methylation inhibition by SAH, calculated from the results of the left panel FIG. 19.

Specifically, the assay for measuring histone methyltransferase activity was carried out by the same method as the method using G9a as a peptidase in Example 8 except for using S-Adenosyl-L-homocysteine (SAH) in place of gliotoxin. SAH is a by-product of the methylation reaction and is known to inhibit histone methyltransferase in a negative feedback manner. The results of the assay for measuring histone methyltransferase activity are shown in FIG. 19. The results in the left panel of FIG. 19 showed that the fluorescence intensity of AMC (that is, the degree of the inhibition of peptidyl MCA methylation) increased as the concentration of SAH was increased. The rate (%) of the inhibition of methylation by SAH was calculated from the results in the left panel of FIG. 19. The results are shown in the right panel of FIG. 19. These results showed that the $IC_{50}$ of SAH for G9a was 0.49 mM. This demonstrated that the assay for measuring histone methyltransferase activity could also sensitively evaluate the inhibitory activity of the low molecular compound.

EXAMPLE 10

[Fluorescence Spectrum for Substrate compound of the Present Invention Containing MCA and AMC]

To construct a more sensitive measurement assay system, the analysis of fluorescence spectra for the substrate compound of the present invention (BocLys(Me)$_n$MCA) and AMC was attempted. Specifically, it was carried out by the following method.

Figure 20:
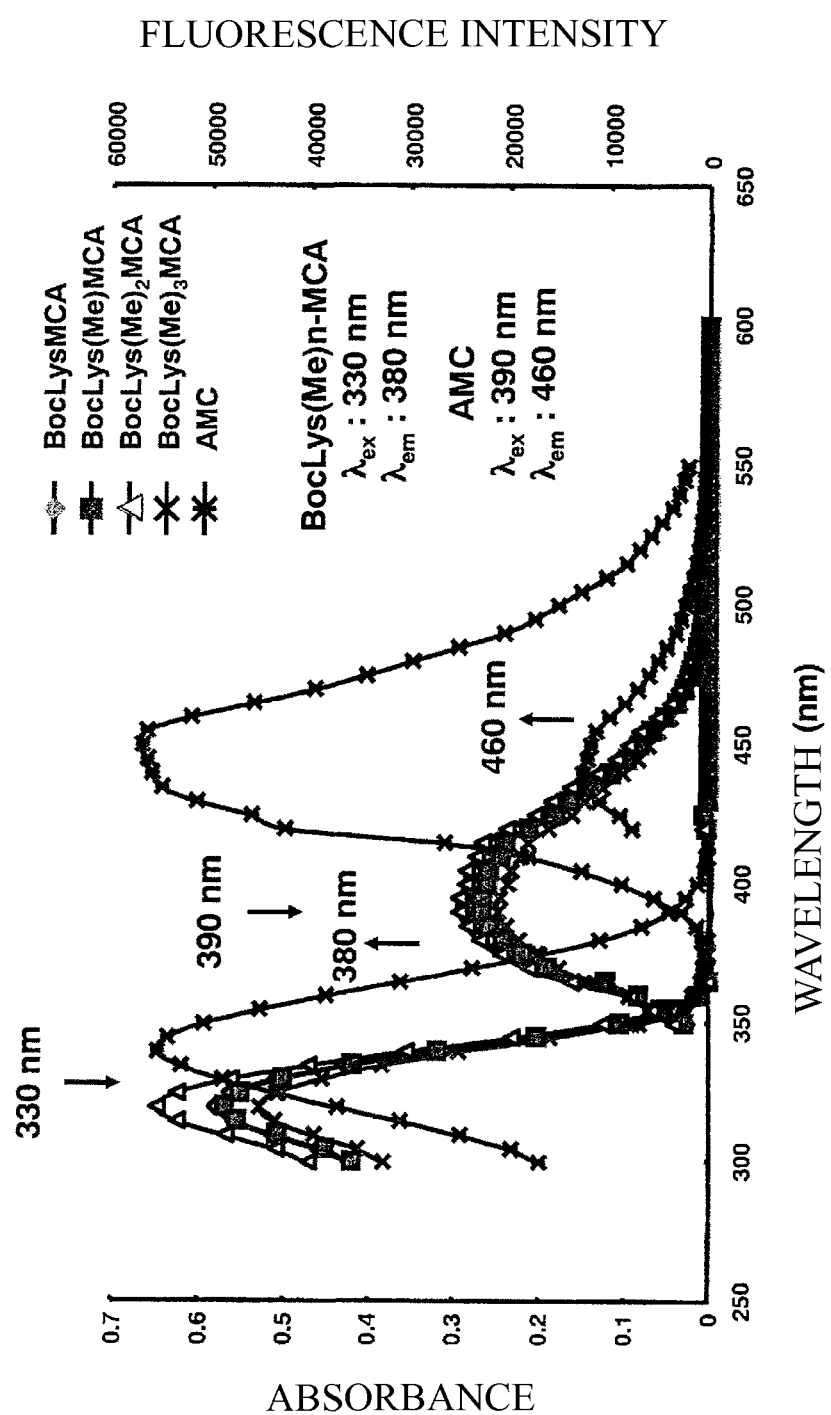
FIG. 20 is a graph showing the absorption spectra and fluorescence spectra of BocLys (Me)$_n$MCA (n=0, 1, 2, or 3) and AMC.

1 μL of BocLys(Me)MCA (2 mM) and 49 μL of distilled water were mixed to prepare a mixed solution. Using BocLys (Me)$_2$MCA, BocLys(Me)$_2$MCA, or AMC in place of BocLys (Me)MCA, a mixed solution was similarly prepared. The results of measuring the absorption spectrum and the fluorescence spectrum for each mixed solution are shown in FIG. 20. As shown in FIG. 20, the maximum absorption wavelength of BocLys(Me)$_n$MCA was 320 nm, and 330 nm was included in the absorption wavelength region thereof but 390 nm was not included therein. The maximum fluorescence wavelength of BocLys(Me)$_n$MCA was 395 nm, and 380 nm was included in the fluorescence wavelength region thereof. The maximum absorption wavelength of AMC was 340 nm, and 330 nm was included in the absorption wavelength region thereof and 390 nm was also included therein although the degree of absorption was low thereat. The maximum fluorescence wavelength of AMC was 450 nm, and 460 nm was included in the maximum fluorescence wavelength region and almost no wavelength of 380 nm or less was included therein. These results showed that although AMC was inevitably excited contemporaneously with BocLys(Me)$_n$MCA when light of 330 nm was irradiated, only the fluorescence of BocLys(Me)$_n$MCA could be detected without detecting the fluorescence of AMC if fluorescence was captured at 380 nm not included in the fluorescence wavelength of AMC. The results of FIG. 20 showed that when light of 390 nm was irradiated, BocLys (Me)$_n$MCA was not excited since the wavelength was not included in the absorption wavelength thereof and did not emit fluorescence although AMC was excited since the wavelength was included in the absorption wavelength thereof and emitted fluorescence, resulting in enabling the detection of only AMC at a desired fluorescence wavelength (e.g., 460 nm) of AMC.

Figure 21:
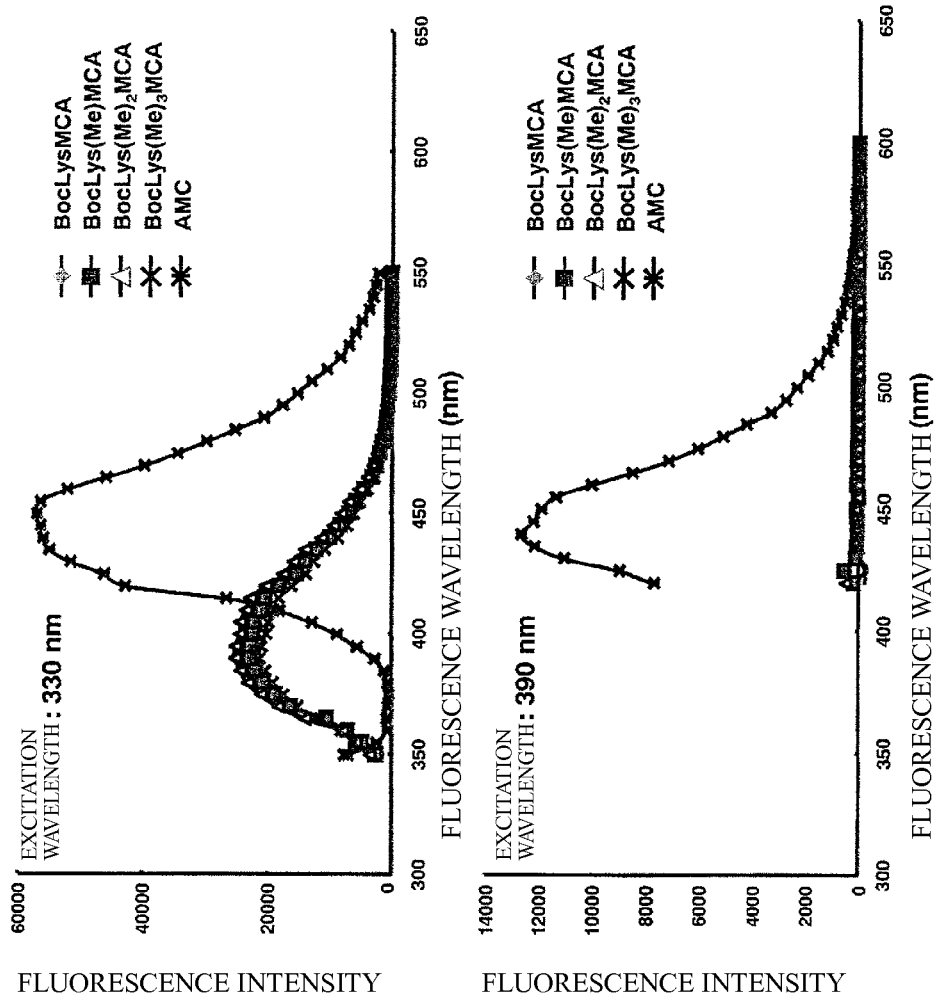
FIG. 21 is a pair of graphs showing the fluorescence spectra of BocLys (Me)$_n$MCA (n=0, 1, 2, 3) and AMC.

The figure obtained by removing the waveforms of the absorption spectra from the graph of FIG. 20 and separating the resultant graph into the case where the excitation wavelength was 330 nm and the case where it was 390 nm is shown in FIG. 21. Specifically, for each of the above mixed solutions, the results of measuring the fluorescence intensity of each of the above mixed solutions at an excitation wavelength (λex) of 330 nm and fluorescence wavelengths (λem) of 350 to 550 nm are shown in the upper panel of FIG. 21 and the results of measuring the fluorescence intensity thereof at an excitation wavelength (λex) of 390 nm and fluorescence wavelengths (λem) of 420 to 600 nm are shown in the lower panel of FIG. 21. It will also be seen from the upper panel of FIG. 21 that although AMC is inevitably excited contemporaneously with BocLys(Me)$_n$MCA when light of 330 nm was irradiated, only the fluorescence of BocLys(Me)$_n$MCA could be detected without detecting the fluorescence of AMC if fluorescence was captured at 380 nm not included in the fluorescence wavelength of AMC. It will also be seen from the lower panel of FIG. 21 that when light of 390 nm was irradiated, BocLys(Me)$_n$MCA was not excited since the wavelength was not included in the absorption wavelength thereof and did not emit fluorescence although AMC was excited since the wavelength was included in the absorption wavelength thereof and emitted fluorescence, resulting in enabling the detection of only AMC at a desired fluorescence wavelength (e.g., 460 nm) of AMC.

EXAMPLE 11

[Decreased Susceptibility to Peptidase Due to Methylation of Substrate Compound of the Present Invention—2]

It is as shown by the mixing assay between the substrate compound of the present invention and a peptidase in the above-described Example 1 that the methylation of the substrate compound of the present invention actually decreases susceptibility to the peptidase. In the mixing assay, histone methyltransferase was measured using the amount of the decrease of the fluorescence intensity of AMC separated from the unmethylated substrate compound as an indicator. Accordingly, a mixing assay was carried out in order to examine whether the measurement was also possible using the amount of the increase of the fluorescence intensity of MCA in a methylated substrate compound as an indicator.

Distilled water was added to 10 μL of 2×HMT buffer (100 mM Tris-HCl (pH 8.5), 20 mM MgCl$_2$, 40 mM KCl, 20 mM 2-mercaptoethanol, 500 mM sucrose) and 1 μL of a BocLysMCA solution to adjust the total volume to 20 μL. To the resultant solution was added 30 μL of a peptidase solution (20 mg/mL trypsin), which was then mixed and incubated at 37° C. for 15 minutes. Then, the fluorescence intensity of the solution was measured at an excitation wavelength (λex) of 330 nm and a fluorescence wavelength (λem) of 380 nm. The wavelength is a wavelength for detecting only the fluorescence of BocLys(Me)$_n$MCA without detecting the fluorescence of AMC as shown in the above-described Example 10. The mixing assay was carried out by the same method as the above-described method except for using BocLys(Me)MCA, BocLys(Me)$_2$ MCA, or BocLys(Me)$_3$MCA in place of BocLysMCA, and the fluorescence intensity of the MCA group was similarly measured. A solution containing no BocLys(Me)$_n$MCA was also measured for the fluorescence intensity. These results are shown in the right panel of FIG. 22. For comparison, the results of measuring the fluorescence intensity of the same solution at an excitation wavelength (λex) of 390 nm and a fluorescence wavelength (λem) of 460 nm in the above-described Example (left panel of FIG. 7) is shown in the left panel of FIG. 22.

Figure 22:
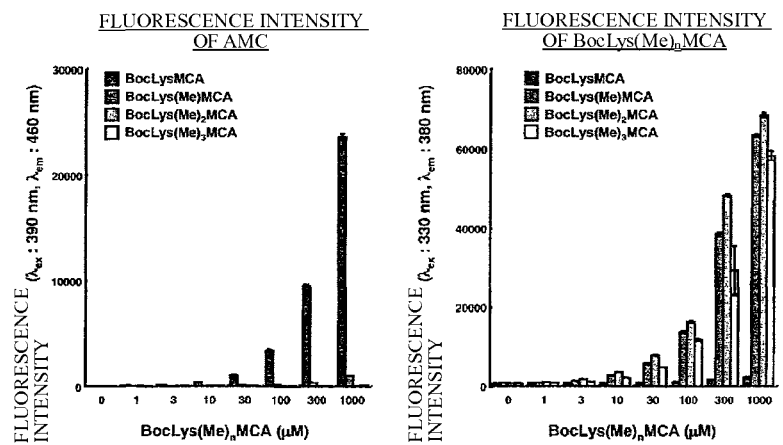
FIG. 22 is a pair of graphs showing the results of a test confirming decreased susceptibility to trypsin due to the methylation of BocLys (Me)$_n$MCA. The left panel of FIG. 22 shows the results of measuring the fluorescence intensity of AMC, and the right panel shows the results of measuring the fluorescence intensity of BocLys(Me)$_n$MCA (n=0, 1, 2, 3).

BocLysMCA is cleaved by trypsin to form BocLys and AMC (FIG. 6); thus, the fluorescence intensity of AMC released in a manner dependent on the concentration of BocLysMCA increased (left panel of FIG. 22). In contrast, methylated BocLysMCA (BocLys(Me)$_n$MCA) is not cleaved by trypsin (FIG. 6); thus, the fluorescence intensity of AMC did not increase (left panel of FIG. 22) and the fluorescence intensity of the remaining methylated BocLysMCA increased in a manner dependent on the concentration thereof (right panel of FIG. 22). As shown in the right panel of FIG. 22, then, fluorescence intensity could be measured at an excitation wavelength (λex) of 330 nm and a fluorescence wavelength (λem) of 380 nm to measure the methylated BocLysMCA sensitively.

In a mixing assay using a peptidase solution (20 mAU/mL lysyl endopeptidase) in place of the peptidase solution (20 mg/mL trypsin) in the above-described mixing assay, the fluorescence intensity of MCA of each solution was measured at an excitation wavelength (λex) of 330 nm and a fluorescence wavelength (λem) of 380 nm. The results are shown in the right panel of FIG. 23. For comparison, the results of measuring the fluorescence intensity of AMC in each solution at an excitation wavelength (λex) of 390 nm and a fluorescence wavelength (λem) of 460 nm in the above-described Example 1 (right panel of FIG. 7) are shown in the left panel of FIG. 23.

Figure 23:
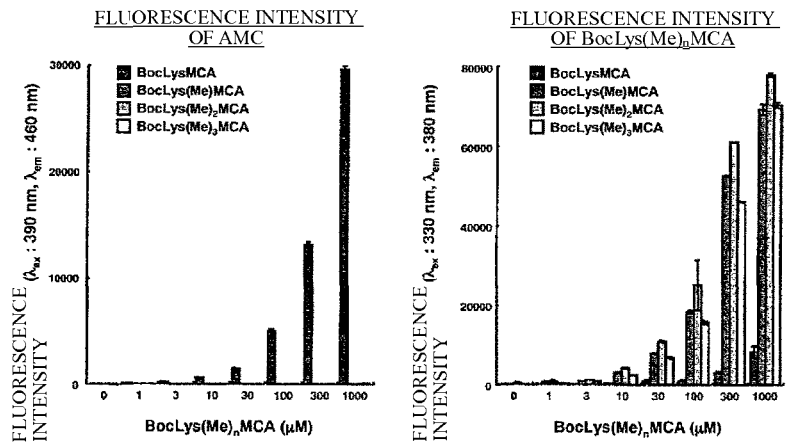
FIG. 23 is a pair of graphs showing the results of a test confirming decreased susceptibility to lysyl endopeptidase due to the methylation of BocLys (Me)$_n$MCA. The left panel of FIG. 23 shows the results of measuring the fluorescence intensity of AMC, and the right panel shows the results of measuring the fluorescence intensity of BocLys(Me)$_n$MCA (n=0, 1, 2, 3).

As in the right panel of FIG. 22, fluorescence intensity could be measured at an excitation wavelength (λex) of 330 nm and a fluorescence wavelength (λem) of 380 nm to measure methylated BocLysMCA sensitively (right panel of FIG. 23). In other words, it was shown that the decreased susceptibility to peptidase due to the methylation of the substrate compound of the present invention could be sensitively evaluated using the amount of the increase of the fluorescence intensity of MCA in a methylated peptidyl MCA rather than the amount of the decrease of the fluorescence intensity of AMC as an indicator.

EXAMPLE 12

[Detection of BocLysMCA and AMC Using Difference of Fluorescence Wavelength]

It is as shown in the above-described Example 10 that the excitation wavelength and the fluorescence wavelength can be adjusted to detect only BocLysMCA or only AMC. A fluorescence measurement assay was carried out in order to examine whether only BocLysMCA or only AMC could be detected even in the case of a mixed solution of BocLysMCA and AMC.

2 μL of BocLysMCA (2 mM) and 48 μL of distilled water were mixed to prepare 50 μL of a solution (BocLysMCA 40 μM). 1 μL of BocLysMCA (2 mM), 1 μL of AMC (2 mM), and 48 μL of distilled water were also mixed to prepare 50 μL of a solution (BocLysMCA 20 μM+AMC 20 μM). 2 μL of AMC (2 mM) and 48 μL of distilled water were mixed to prepare 50 μL of a solution (40 μM) (AMC 40 μM).

Figure 24:
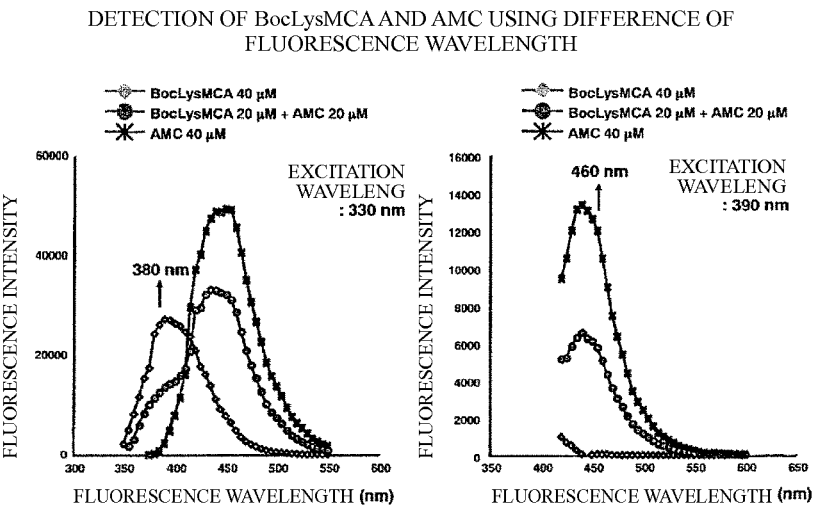
FIG. 24 is a pair of graphs showing the fluorescence spectra of a mixed solution of BocLysMCA and AMC. The left panel of FIG. 24 shows the results of measurement at an excitation wavelength (λex) of 330 nm and a fluorescence wavelength (λem) of 380 nm, and the right panel shows the results of measurement at an excitation wavelength (λex) of 390 nm and a fluorescence wavelength (λem) of 460 nm.

The results of measuring the fluorescence intensity of these 3 solutions at an excitation wavelength (λex) of 330 nm and fluorescence wavelengths (λem) of 350 to 550 nm are shown in the left panel of FIG. 24, and the results of measuring that at an excitation wavelength (λex) of 390 nm and fluorescence wavelengths (λem) of 420 to 600 nm are shown in the right panel of FIG. 24. The results of FIG. 24 showed that the concentration of BocLysMCA or AMC even in the mixture of BocLysMCA and AMC could be quantitatively measured by measurement at the respective specific excitation wavelengths and fluorescence wavelengths, that is, at an excitation wavelength (λex) of 330 nm and a fluorescence wavelength (λem) of 380 nm for BocLysMCA and at an excitation wavelength (λex) of 390 nm and a fluorescence wavelength (λem) of 460 nm for AMC.

EXAMPLE 13

[Examination of Substrate Specificity of Histone Methyltransferase Using Peptidyl MCA—4]

An assay for measuring histone methyltransferase activity was carried out in order to examine whether the evaluation of the substrate specificity of histone methyltransferase using a peptidyl MCA could also be performed using the amount of the increase of the fluorescence intensity of MCA in the peptidyl MCA rather than the amount of the decrease of the fluorescence intensity of AMC as an indicator. Specifically, it was carried out by the following method.

When G9a was adopted as a histone methyltransferase, the following method was used. 10 μL of 2×HMT buffer (100 mM Tris-HCl (pH 8.5), 20 mM MgCl$_2$, 40 mM KCl, 20 mM 2-mercaptoethanol, 500 mM sucrose), 0.4 μL of a BSA solution (150 μg/mL), 4 μL of GST-mG9a (0, 0.025 to 0.75 μg/μL), and 3.6 μL of distilled water were mixed and then incubated at room temperature for 1 hour. Then, 1 μL of SAM (final concentration: 1 mM) and 1 μL, of a peptidyl MCA solution (1.2 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 330 nm and a fluorescence wavelength (λem) of 380 nm or at an excitation wavelength (λex) of 390 nm and a fluorescence wavelength (λem) of 460 nm. The final concentration of GST-mG9a during the measurement of fluorescence intensity was 0, 0.005, 0.015, 0.05, or 0.15 μg/μL.

When Set7/9 was adopted as a histone methyltransferase, the following method was used. 10 μL of 2×HMT buffer (100 mM Tris-HCl (pH 8.5), 20 mM MgCl$_2$, 40 mM KCl, 20 mM 2-mercaptoethanol, 500 mM sucrose), 0.4 μL of a BSA solution (150 μg/mL), 4 L of His-Set7/9 (0, 0.025 to 0.75 μg/μL), and 3.6 μL of distilled water were mixed and then incubated at room temperature for 1 hour. Then, 1 μL of SAM (final concentration: 0.1 mM) and 1 μL of a peptidyl MCA solution (1.2 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 330 nm and a fluorescence wavelength (λem) of 380 nm or at an excitation wavelength (λex) of 390 nm and a fluorescence wavelength (λem) of 460 nm. The final concentration of His-Set7/9 during the measurement of fluorescence intensity was 0, 0.005, 0.015, 0.05, or 0.15 μg/μL.

Figure 25:
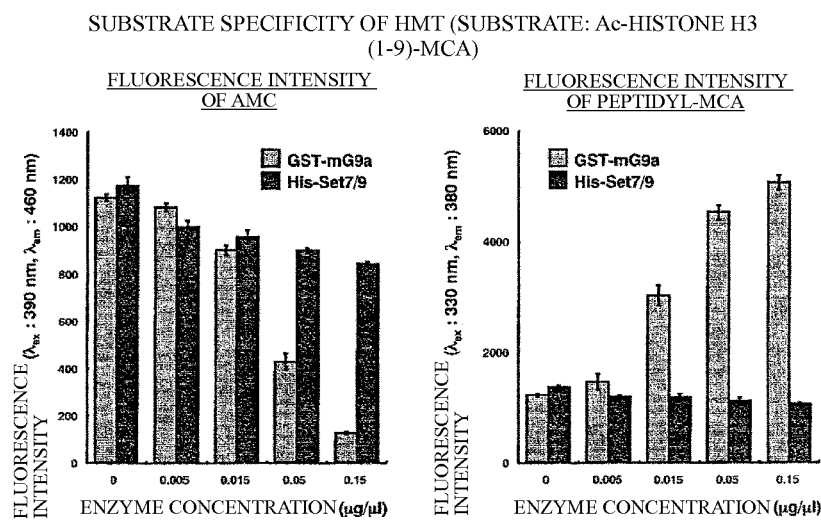
FIG. 25 is a pair of graphs showing the results of an assay for measuring histone methyltransferase activity using a peptidyl MCA (Ac-histone H3 (1-9)-MCA). The left panel of FIG. 25 shows the results of measuring the fluorescence intensity of AMC, and the right panel shows the results of measuring the fluorescence intensity of the peptidyl MCA.

The results of measurement at an excitation wavelength (λex) of 330 nm and a fluorescence wavelength (λem) of 380 nm using Ac-histone H3 (1-9)-MCA as a peptidyl MCA are shown in the right panel of FIG. 25, and the results of measurement at an excitation wavelength (λex) of 390 nm and a fluorescence wavelength (λem) of 460 nm using the peptidyl MCA are shown in the left panel of FIG. 25. The results of measurement at an excitation wavelength (λex) of 330 nm and a fluorescence wavelength (λem) of 380 nm using Ac-ERα(299-302)-MCA as a peptidyl MCA are shown in the right panel of FIG. 26, and the results of measurement at an excitation wavelength (λex) of 390 nm and a fluorescence wavelength (λem) of 460 nm are shown in the left panel of FIG. 26. In each panel of FIGS. 25 and 26, light-colored column graphs represent the results for the use of GST-mG9a, and dark-colored column graphs represent the results for the use of His-Set7/9.

GST-mG9a methylates Ac-histone H3 (1-9)-MCA; thus, the amount of AMC (the fluorescence intensity of AMC) released after adding trypsin decreases in a manner dependent on the concentration of GST-mG9a (left panel of FIG. 25), and the fluorescence intensity of the remaining methylated peptidyl MCA increased (right panel of FIG. 25). In contrast, His-Set7/9 does not methylate Ac-histone H3 (1-9)-MCA; thus, the amount of AMC (the fluorescence intensity of AMC) released after adding trypsin little changed (left panel of FIG. 25) and the fluorescence intensity of the peptidyl MCA also little changed (right panel of FIG. 25).

Figure 26:
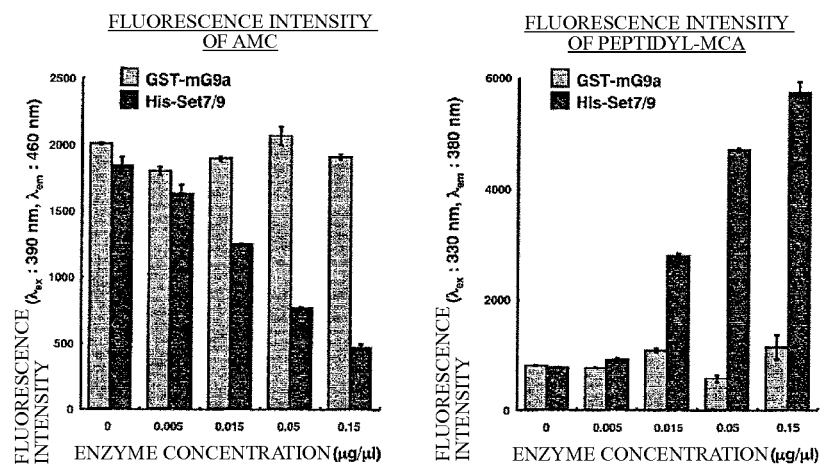
FIG. 26 is a pair of graphs showing the results of an assay for measuring histone methyltransferase activity using a peptidyl MCA (Ac-ERa (299-302)-MCA). The left panel of FIG. 25 shows the results of measuring the fluorescence intensity of AMC, and the right panel shows the results of measuring the fluorescence intensity of the peptidyl MCA.

His-Set7/9 methylates Ac-ERα(299-302)-MCA; thus, the amount of AMC (the fluorescence intensity of AMC) released after adding trypsin decreases in a manner dependent on the concentration of His-Set7/9 (left panel of FIG. 26), and the fluorescence intensity of the remaining methylated peptidyl MCA increased (right panel of FIG. 26). In contrast, GSTmG9a does not methylate Ac-ERα(299-302)-MCA; thus, the amount of AMC (the fluorescence intensity of AMC) released after adding trypsin little changed (left panel of FIG. 26) and the fluorescence intensity of the peptidyl MCA also little changed (right panel of FIG. 26).

As shown in each result in FIGS. 25 and 26, then, fluorescence intensity could be measured at an excitation wavelength (λex) of 330 nm and a fluorescence wavelength (λem) of 380 nm to measure each peptidyl MCAs sensitively. In other words, it was shown that the evaluation of the substrate specificity of histone methyltransferase using each peptidyl MCA could be sensitively performed using the amount of the increase of the fluorescence intensity of MCA in the peptidyl MCA rather than the amount of the decrease of the fluorescence intensity of AMC as an indicator.

EXAMPLE 14

[Activity Evaluation of Histone Methyltransferase Inhibitor Using Peptidyl MCA—3]

An assay for measuring histone methyltransferase activity was carried out in order to examine whether the evaluation of histone methyltransferase activity using a peptidyl MCA could be carried out using the amount of the increase of the fluorescence intensity of MCA in the peptidyl MCA rather than the amount of the decrease of the fluorescence intensity of AMC as an indicator. Specifically, it was carried out by the following method.

When G9a was adopted as a histone methyltransferase, the following method was used. 10 μL of 2×HMT buffer (100 mM Tris-HCl (pH 8.5), 20 mM $MgCl_2$, 40 mM KCl, 20 mM 2-mercaptoethanol, 500 mM sucrose), 0.4 μL of a BSA solution (150 μg/mL), 4 μL of GST-mG9a (0, 0.25 μg/μL), 1 μL of gliotoxin (any of various concentrations), and 2.6 μL of distilled water were mixed and then incubated at room temperature for 1 hour. Then, 1 μL of SAM (20 mM) and 1 μL of a peptidyl MCA (Ac-histone H3 (1-9)-MCA) solution (1.2 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 330 nm and a fluorescence wavelength (λem) of 380 nm or at an excitation wavelength (λex) of 390 nm and a fluorescence wavelength (λem) of 460 nm. The final concentration of GST-mG9a during the measurement of fluorescence intensity was 0 μg/μL or 0.05 μg/μL.

Figure 27:
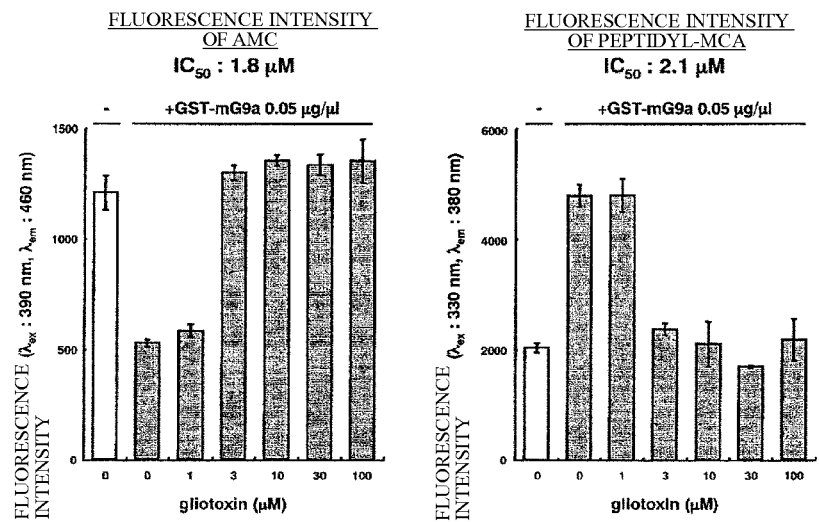
FIG. 27 is a pair of graphs showing the results of activity evaluation of a histone methyltransferase inhibitor (gliotoxin) using a peptidyl MCA and G9a. The left panel of FIG. 27 shows the results of measuring the fluorescence intensity of AMC, and the right panel shows the results of measuring the fluorescence intensity of the peptidyl MCA.

The results of measuring the solution at an excitation wavelength (λex) of 330 nm and a fluorescence wavelength (λem) of 380 nm are shown in the right panel of FIG. 27, and the results of measuring it at an excitation wavelength (λex) of 390 nm and a fluorescence wavelength (λem) of 460 nm are shown in the left panel of FIG. 27. The amount of AMC (the fluorescence intensity of AMC) released after adding trypsin increased when the concentration of gliotoxin was increased (left panel of FIG. 27), and the fluorescence intensity of the remaining methylated peptidyl MCA increased (right panel of FIG. 27). This could determine that gliotoxin inhibited the methylation of G9a. When the $IC_{50}$ of gliotoxin for G9a was calculated from the results in the right panel of FIG. 27, it was found to be 2.8 μM. This value was almost the same as the $IC_{50}$ value (1.8 μM) thereof calculated from the results in the left panel of FIG. 27.

When His-Set7/9 was adopted as a histone methyltransferase, the following method was used. 10 μL of 2×HMT buffer (100 mM Tris-HCl (pH 8.5), 20 mM $MgCl_2$, 40 mM KCl, 20 mM 2-mercaptoethanol, 500 mM sucrose), 0.4 μL of a BSA solution (150 μg/mL), 4 μL of His-Set7/9 (0, 0.25 μg/μL), 1 μL of gliotoxin (any of various concentrations), and 2.6 μL of distilled water were mixed and then incubated at room temperature for 1 hour. Then, 1 μL, of SAM (2 mM) and 1 μL of a peptidyl MCA (Ac-ERα(299-302)-MCA) solution (1.2 mM) were added thereto, which was then incubated at 37° C. for 1 hour. Thereafter, 30 μL of a trypsin solution (20 mg/mL) was added thereto, followed by incubation at 37° C. for 15 minutes. Then, the fluorescence intensity of the solution was measured at an excitation wavelength (λex) of 330 nm and a fluorescence wavelength (λem) of 380 nm or at an excitation wavelength (λex) of 390 nm and a fluorescence wavelength (λem) of 460 nm. The final concentration of His-Set7/9 during the measurement of fluorescence intensity was 0 μg/μL or 0.05 μg/μL.

Figure 28:
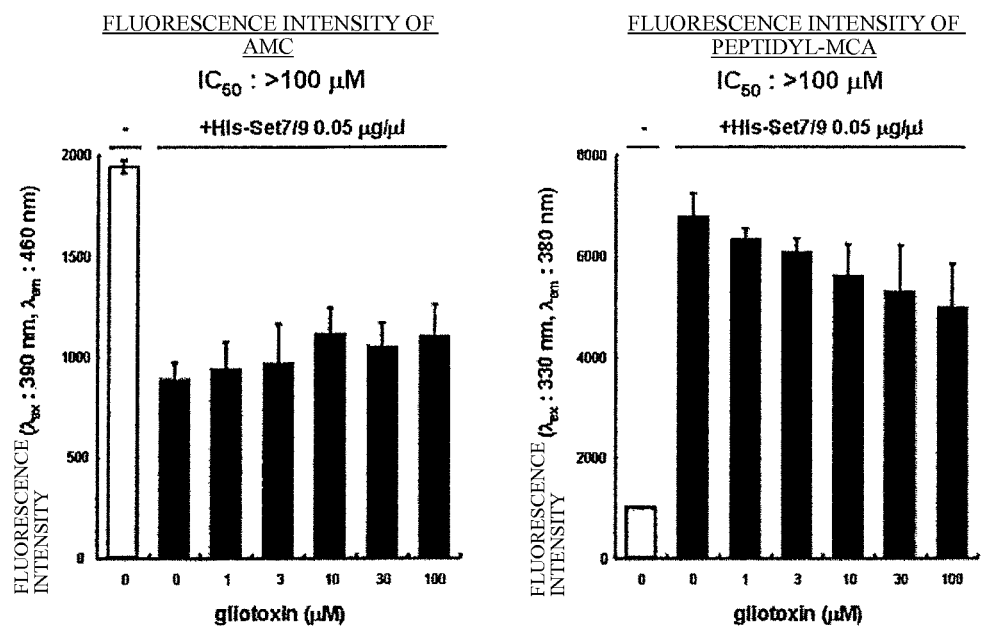
FIG. 28 is a pair of graphs showing the results of activity evaluation of a histone methyltransferase inhibitor (gliotoxin) using a peptidyl MCA and Set7/9. The left panel of FIG. 28 shows the results of measuring the fluorescence intensity of AMC, and the right panel shows the results of measuring the fluorescence intensity of the peptidyl MCA.

The results of measuring the solution at an excitation wavelength (λex) of 330 nm and a fluorescence wavelength (λem) of 380 nm are shown in the right panel of FIG. 28, and the results of measuring it at an excitation wavelength (λex) of 390 nm and a fluorescence wavelength (λem) of 460 nm are shown in the left panel of FIG. 28. Gliotoxin does not inhibit the methylation of G9a; thus, the increased concentration of gliotoxin poorly changed the amount of AMC (the fluorescence intensity of AMC) released after adding trypsin (left panel of FIG. 28) and also poorly changed the fluorescence intensity of the remaining methylated peptidyl MCA (right panel of FIG. 28). This could determine that gliotoxin did not inhibit the methylation of G9a. When the $IC_{50}$ of gliotoxin for His-Set7/9 was calculated from the results in the right panel of FIG. 28, it was shown to be higher than 100 μM. This value was the same as the $IC_{50}$ value (>100 μM) thereof calculated from the results in the left panel of FIG. 27.

The results of FIGS. 27 and 28 showed that the evaluation of the activity of histone methyltransferase inhibitor using each peptidyl MCA could be sensitively performed using the amount of the increase of the fluorescence intensity of MCA in the peptidyl MCA rather than the amount of the decrease of the fluorescence intensity of AMC as an indicator.

(Summary of the Present Invention)

Figure 29:
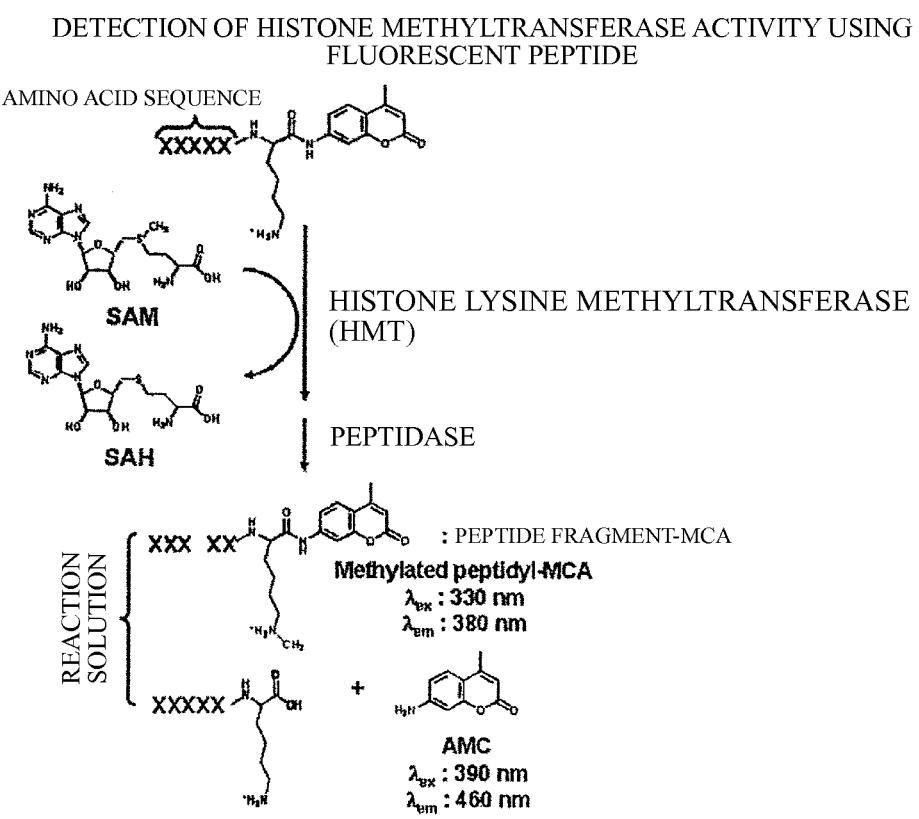
FIG. 29 is a diagram showing an outline of detection of histone methyltransferase activity using a peptidyl MCA.

FIG. 29 shows the contents in which a preferred aspect of the method for measuring histone methyltransferase activity according to the present invention is summarized taking for example a case where a peptidyl MCA was used as the substrate compound or the like of the present invention with trypsin being used as a peptidase. The contact of a sample containing histone methyltransferase with a peptidyl MCA typically results in the methylation of lysine of a part of the peptidyl MCA, which leads to a state in which the methylated peptidyl MCA and the unmethylated peptidyl MCA co-exist in the reaction solution. A large excess of trypsin is added to this reaction solution. Because trypsin cannot act on the "methylated peptidyl MCA", the "methylated peptidyl MCA" is left in the reaction solution. However, strictly, when a trypsin cleavage site is contained in the peptide portion of the "methylated peptidyl MCA", a molecule resulting from cleavage at the cleavage site also co-exist; however, the molecule is also conveniently indicated herein without particular distinction as a "methylated peptidyl MCA".

In contrast, trypsin can act on the "unmethylated peptidyl MCA" and produces the formation of "AMC" and the "unmethylated peptide". When a trypsin cleavage site is contained in the peptide portion of the unmethylated peptide, a molecule resulting from cleavage at the cleavage site will also co-exist. It is as described in the above-described Example 5 (FIGS. 11 and 12) that the "unmethylated peptidyl MCA" is not left in the reaction solution on which trypsin is caused to sufficiently act. Accordingly, any of the "unmethylated peptidyl MCA" and "AMC" co-existing in the reaction solution can be selectively quantitated to calculate the degree of the raise of the methylation level of the peptidyl MCA from the amount of the increase of the fluorescence intensity of the MCA group of the "methylated peptidyl MCA" or the amount of the decrease of the fluorescence intensity of "AMC" to evaluate the degree of the raise as the degree of histone methyltransferase activity in the sample.

INDUSTRIAL APPLICABILITY

The present invention can be suitably used in the field for the measurement of histone methyltransferase activity and in the field for screening for compounds inhibiting histone methyltransferase activity. In addition, the present invention can be used to examine the substrate specificity of a particular histone methyltransferase or to examine a histone methyltransferase specific for a particular peptide. A compound inhibiting histone methyltransferase activity obtained by the screening method of the present invention is expected as a therapeutic agent for diseases such as cancer and neurodegenerative disease and to be applied to regenerative medicine using iPS cells.

The invention claimed is:

1. A method for measuring histone methyltransferase activity in a sample, comprising the steps of:
   (a) providing a substrate compound represented by the following general formula (I):

$$R_1-X-K-R_2 \qquad (I)$$

or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue),
   wherein the cleavage of the amide bond by peptidase changes the fluorescence property or chromogenic property of the dye label, and the methylation of the ε amino group of the lysine residue by the histone methyltransferase decreases susceptibility to peptidase;
   (b) contacting the substrate compound represented by the general formula (I) or a salt thereof with a sample under conditions required for methylation reaction by the histone methyltransferase;
   (c) exposing the substrate compound or a salt thereof to peptidase after the step (b);
   (d) measuring the degree of the change of the fluorescence property or chromogenic property of the dye label after the step (c) compared to the fluorescence property or chromogenic property of a dye label in a control to calculate the degree of the increase of the methylation level of the substrate compound or a salt thereof, based on the degree of the decrease of the cleavage activity of the peptidase that uses the substrate compound or a salt thereof as a substrate; and
   (e) evaluating the degree of the increase of the methylation level in the step (d) as the degree of histone methyltransferase activity in the sample,
   wherein the control is the substrate compound represented by the general formula (I) or a salt thereof exposed to peptidase while not contacting the sample under conditions required for methylation reaction by the histone methyltransferase.

2. The method according to claim 1, wherein the measurement of the degree of the change of the fluorescence property or chromogenic property of the dye label in the step (d) is performed by:
   measuring the dye label whose fluorescence property or chromogenic property has been changed by the cleavage of the amide bond in the substrate compound or a salt thereof by peptidase; or
   measuring the dye label in which the amide bond has not been cleaved by peptidase because of the methylation of the ε amino group of a lysine residue in the substrate compound or a salt thereof.

3. The method according to claim 2, wherein the peptidase is at least one peptidase selected from the group consisting of lysyl endopeptidase, endoproteinase Lys-C, plasmin, calpain, and trypsin.

4. The method according to claim 1, wherein the peptidase is at least one peptidase selected from the group consisting of lysyl endopeptidase, endoproteinase Lys-C, plasmin, calpain, and trypsin.

5. A method for screening for compounds that inhibit histone methyltransferase activity, comprising the steps of:
   (a) providing a substrate compound represented by the following general formula (I):

$$R_1-X-K-R_2 \qquad (I)$$

or a salt thereof (wherein $R_1$ represents a hydrogen atom or a protecting group for an amino terminus; X represents a peptide consisting of 0 or 1 or more amino acid residues; K represents a lysine residue; and $R_2$ represents a dye label linked via an amide bond to the carbonyl terminus of a lysine residue),
   wherein the cleavage of the amide bond by peptidase changes the fluorescence property or chromogenic property of the dye label, and the methylation of the ε amino group of the lysine residue by the histone methyltransferase decreases susceptibility to peptidase;
   (b) contacting the substrate compound represented by the general formula (I) or a salt thereof with the histone methyltransferase in the presence of a test compound under conditions required for methylation reaction by the histone methyltransferase;
   (c) exposing the substrate compound or a salt thereof to peptidase after the step (b);
   (d) measuring the degree of the change of the fluorescence property or chromogenic property of the dye label after the step (c) compared to the fluorescence property or chromogenic property of a dye label in a control to calculate the degree of the increase of the methylation level of the substrate compound or a salt thereof, based on the degree of the decrease of the cleavage activity of the peptidase that uses the substrate compound or a salt thereof as a substrate; and
   (e) selecting a test compound for which the degree of the increase of the methylation level of the substrate compound or a salt thereof in the step (d) is low compared to the degree of the increase of the methylation level of the control,
   wherein the control is the substrate compound represented by the general formula (I) or a salt thereof exposed to peptidase after contacting the histone methyltransferase in the absence of the test compound under conditions required for methylation reaction by the histone methyltransferase.

6. The method according to claim 5, wherein the peptidase is at least one peptidase selected from the group consisting of lysyl endopeptidase, endoproteinase Lys-C, plasmin, calpain, and trypsin.

* * * * *